(12) United States Patent
Yurek et al.

(10) Patent No.: US 12,256,989 B2
(45) Date of Patent: Mar. 25, 2025

(54) TOOL GUIDING DEVICE FOR KIDNEY STONE TREATMENT APPARATUS

(71) Applicant: CALYXO, INC., Pleasanton, CA (US)

(72) Inventors: Matthew Yurek, San Diego, CA (US); Ling Tong, Fremont, CA (US); Brian Y. Tachibana, Pleasanton, CA (US); Thomas R. Jenkins, Pleasanton, CA (US); Calvin Lam, Pleasanton, CA (US); Ailee Pham, Pleasanton, CA (US); Kejin Wang, Dublin, CA (US); Joseph Catanese, III, Oakland, CA (US); Jee Shin, Pleasanton, CA (US); Caralin Riva Adair, Santa Rosa, CA (US); Andrew J. Hudson, Santa Rosa, CA (US)

(73) Assignee: CALYXO, INC., Pleasanton, CA (US)

( * ) Notice: Subject to any disclaimer, the term of this patent is extended or adjusted under 35 U.S.C. 154(b) by 0 days.

(21) Appl. No.: 18/827,597

(22) Filed: Sep. 6, 2024

(65) Prior Publication Data
US 2024/0423715 A1   Dec. 26, 2024

Related U.S. Application Data

(63) Continuation of application No. 18/373,229, filed on Sep. 26, 2023.

(Continued)

(51) Int. Cl.
*A61B 18/26* (2006.01)
*A61B 18/00* (2006.01)
*A61B 18/20* (2006.01)

(52) U.S. Cl.
CPC .... *A61B 18/26* (2013.01); *A61B 2018/00166* (2013.01); *A61B 2018/00196* (2013.01);
(Continued)

(58) Field of Classification Search
CPC .......... A61B 18/26; A61B 2018/00166; A61B 2018/00196; A61B 2018/00511;
(Continued)

(56) References Cited

U.S. PATENT DOCUMENTS

| 3,065,749 A | 11/1962 | Brass |
| 3,438,607 A | 4/1969 | Williams et al. |

(Continued)

FOREIGN PATENT DOCUMENTS

| CN | 203776869 U | 8/2014 |
| CN | 203776946 U | 8/2014 |

(Continued)

OTHER PUBLICATIONS

Ali, et al. "Retrograde Cystonephroscopy for Cmoplex Renal Calculi Using Novel Dual-Action Aspiration, Irrigation Cystoscope: Initial Case Series", Journal of Endourology; Jul. 2022; vol. 36 (7); pp. 898-905.

(Continued)

*Primary Examiner* — Scott M. Getzow
(74) *Attorney, Agent, or Firm* — Squire Patton Boggs (US) LLP

(57) ABSTRACT

A catheter assembly is provided having a working lumen and a guide. The guide is configured to position a fragmentizing device within the working lumen. The guide is configured to prevent or minimize any unintended movement of a distal section of the fragmentizing device within the working lumen when the distal section of the fragmentizing device is positioned at a distal end of the working lumen.

26 Claims, 15 Drawing Sheets

Related U.S. Application Data

(60) Provisional application No. 63/411,568, filed on Sep. 29, 2022.

(52) U.S. Cl.
CPC ............ *A61B 2018/00511* (2013.01); *A61B 2018/00625* (2013.01); *A61B 2018/2015* (2013.01); *A61B 2218/002* (2013.01); *A61B 2218/007* (2013.01); *A61B 2560/04* (2013.01)

(58) Field of Classification Search
CPC .. A61B 2018/00625; A61B 2018/2015; A61B 2218/002; A61B 2218/007; A61B 2560/04

See application file for complete search history.

(56) References Cited

U.S. PATENT DOCUMENTS

| | | |
|---|---|---|
| 3,749,090 A | 7/1973 | Stewart |
| 3,830,240 A | 8/1974 | Antonevich et al. |
| 4,146,300 A | 3/1979 | Kaiser |
| 4,203,430 A | 5/1980 | Takahashi |
| 4,215,476 A | 8/1980 | Armstrong |
| 4,294,233 A | 10/1981 | Takahashi |
| 4,295,464 A | 10/1981 | Shihata |
| 4,393,872 A | 7/1983 | Reznik et al. |
| 4,418,688 A | 12/1983 | Loeb |
| 4,458,877 A | 7/1984 | Holmes |
| 4,483,326 A | 11/1984 | Yamaka et al. |
| 4,519,385 A | 5/1985 | Atkinson et al. |
| 4,630,598 A | 12/1986 | Bonnet |
| 4,648,871 A | 3/1987 | Jacob |
| 4,655,197 A | 4/1987 | Atkinson |
| 4,662,871 A | 5/1987 | Rafelson |
| 4,680,026 A | 7/1987 | Weightman et al. |
| 4,688,555 A | 8/1987 | Wardle |
| 4,696,669 A | 9/1987 | Menhusen |
| 4,706,656 A | 11/1987 | Kuboto |
| 4,708,717 A | 11/1987 | Deane et al. |
| 4,802,461 A | 2/1989 | Cho |
| 4,852,551 A | 8/1989 | Opie et al. |
| 4,874,360 A | 10/1989 | Goldberg et al. |
| 4,941,872 A | 7/1990 | Felix et al. |
| 4,950,265 A | 8/1990 | Taylor |
| 4,995,872 A | 2/1991 | Ferrara |
| 4,996,974 A | 3/1991 | Ciarlei |
| 5,057,080 A | 10/1991 | Takahashi |
| 5,095,889 A | 3/1992 | Weissmuller et al. |
| 5,120,305 A | 6/1992 | Boehringer et al. |
| 5,156,142 A | 10/1992 | Anapliotis et al. |
| 5,186,714 A | 2/1993 | Boudreault et al. |
| 5,191,881 A | 3/1993 | Beck |
| 5,226,885 A | 7/1993 | Takahashi |
| 5,230,704 A | 7/1993 | Moberg et al. |
| 5,258,006 A * | 11/1993 | Rydell ............... A61B 18/1442 606/49 |
| 5,263,938 A | 11/1993 | Orr et al. |
| 5,265,840 A | 11/1993 | Gillespie et al. |
| 5,273,524 A | 12/1993 | Fox et al. |
| 5,281,212 A | 1/1994 | Savage et al. |
| 5,295,956 A | 3/1994 | Bales et al. |
| 5,300,043 A | 4/1994 | Devlin et al. |
| 5,307,803 A | 5/1994 | Matsuura et al. |
| 5,312,327 A | 5/1994 | Bales et al. |
| 5,312,332 A | 5/1994 | Bales et al. |
| 5,312,400 A | 5/1994 | Bales et al. |
| 5,314,406 A | 5/1994 | Arias et al. |
| 5,318,541 A | 6/1994 | Viera et al. |
| 5,336,172 A | 8/1994 | Bales et al. |
| 5,336,220 A | 8/1994 | Ryan et al. |
| 5,350,356 A | 9/1994 | Bales et al. |
| 5,354,291 A | 10/1994 | Bales et al. |
| 5,429,596 A | 7/1995 | Arias et al. |
| 5,476,450 A | 12/1995 | Ruggio |
| 5,484,402 A | 1/1996 | Saravia et al. |
| 5,512,035 A | 4/1996 | Konstorum et al. |
| 5,512,045 A | 4/1996 | Gurchumelidze |
| 5,549,547 A | 8/1996 | Cohen et al. |
| 5,579,779 A | 12/1996 | Humphrey |
| 5,588,634 A | 12/1996 | Nettekoven |
| 5,607,420 A | 3/1997 | Schuman |
| 5,609,573 A | 3/1997 | Sandock |
| 5,643,304 A | 7/1997 | Schechter et al. |
| 5,658,258 A | 8/1997 | Kneer et al. |
| 5,776,096 A | 7/1998 | Fields |
| 5,827,229 A | 10/1998 | Auth et al. |
| 5,830,214 A | 11/1998 | Flom et al. |
| 5,836,909 A | 11/1998 | Cosmescu |
| 5,885,228 A | 3/1999 | Rosenman et al. |
| 5,885,288 A | 3/1999 | Aust et al. |
| 5,944,690 A | 8/1999 | Falwell et al. |
| 5,961,485 A | 10/1999 | Martin |
| 5,980,504 A | 11/1999 | Sharkey et al. |
| 6,066,150 A | 5/2000 | Gonon |
| 6,168,577 B1 | 1/2001 | Niederjohn et al. |
| 6,179,807 B1 | 1/2001 | Henniges et al. |
| 6,213,970 B1 | 4/2001 | Nelson et al. |
| 6,328,730 B1 | 12/2001 | Harkrider |
| 6,358,200 B1 | 3/2002 | Grossi |
| 6,471,639 B2 | 10/2002 | Rudischhauser et al. |
| 6,551,281 B1 | 4/2003 | Raulerson et al. |
| 6,623,445 B1 | 9/2003 | Nelson et al. |
| 6,635,028 B1 | 10/2003 | Ielpo et al. |
| 6,645,140 B2 | 11/2003 | Brommersma et al. |
| 6,755,806 B1 | 6/2004 | Von Casimir |
| 6,776,765 B2 | 8/2004 | Soukup et al. |
| 6,827,701 B2 | 12/2004 | MacMahon et al. |
| 6,830,556 B2 | 12/2004 | Harmon et al. |
| 6,857,617 B2 | 2/2005 | Forberg |
| 6,887,221 B1 | 5/2005 | Baillargeon et al. |
| 6,929,236 B1 | 8/2005 | Height et al. |
| 6,932,788 B2 | 8/2005 | Kamiyama et al. |
| 6,939,369 B2 | 9/2005 | Osborne et al. |
| 6,960,189 B2 | 11/2005 | Bates et al. |
| 6,969,368 B2 | 11/2005 | Anspach et al. |
| 6,997,867 B2 | 2/2006 | Soble et al. |
| 7,004,931 B2 | 2/2006 | Hogendijk |
| 7,025,720 B2 | 4/2006 | Boebel et al. |
| 7,179,269 B2 | 2/2007 | Welch et al. |
| 7,249,602 B1 | 7/2007 | Emanuel |
| 7,297,133 B2 | 11/2007 | Nelson et al. |
| 7,465,288 B2 | 12/2008 | Dudney et al. |
| 7,500,947 B2 | 3/2009 | Kucklick et al. |
| 7,503,893 B2 | 3/2009 | Kucklick |
| 7,530,976 B2 | 5/2009 | MacMahon et al. |
| 7,540,868 B2 | 6/2009 | Elliott et al. |
| 7,571,889 B2 | 8/2009 | Miyahara |
| 7,802,574 B2 | 9/2010 | Schultz |
| 7,810,784 B2 | 10/2010 | Abe et al. |
| 7,846,126 B2 | 12/2010 | Steen et al. |
| 7,857,770 B2 | 12/2010 | Raulerson et al. |
| 7,883,516 B2 | 2/2011 | Huang et al. |
| 7,935,049 B2 | 5/2011 | Michel et al. |
| 7,947,039 B2 | 5/2011 | Sartor |
| 7,972,282 B2 | 7/2011 | Clark et al. |
| 8,002,732 B2 | 8/2011 | Vicsonti |
| 8,052,607 B2 | 11/2011 | Byrd |
| 8,062,214 B2 | 11/2011 | Shener et al. |
| 8,118,731 B2 | 2/2012 | Kucklick et al. |
| 8,123,676 B2 | 2/2012 | Kucklick |
| 8,192,500 B2 | 6/2012 | Chung |
| 8,226,548 B2 | 7/2012 | Kucklick |
| 8,241,278 B2 | 8/2012 | Sartor |
| 8,313,081 B2 | 11/2012 | Adelberg |
| 8,353,860 B2 | 1/2013 | Boulais et al. |
| 8,419,626 B2 | 4/2013 | Shener-Irmakoglu et al. |
| 8,454,536 B2 | 6/2013 | Raulerson et al. |
| 8,460,182 B2 | 6/2013 | Ouyang et al. |
| 8,475,453 B2 | 7/2013 | Marczyk et al. |
| 8,613,735 B2 | 12/2013 | Omeda et al. |
| 8,672,928 B2 | 3/2014 | Liu et al. |
| 8,702,681 B2 | 4/2014 | Douglas et al. |
| 8,721,595 B2 | 5/2014 | Stiehl et al. |

(56) References Cited

U.S. PATENT DOCUMENTS

| | | |
|---|---|---|
| 8,740,773 B2 | 6/2014 | Kucklick et al. |
| 8,808,168 B2 | 8/2014 | Ettwein et al. |
| 8,845,521 B2 | 9/2014 | Maruyama |
| D715,921 S | 10/2014 | Wan |
| 8,858,569 B2 | 10/2014 | Wan |
| 8,870,748 B2 | 10/2014 | Kucklick |
| 8,888,683 B2 | 11/2014 | Mejia |
| 8,894,601 B2 | 11/2014 | Moehle et al. |
| 8,945,093 B2 | 2/2015 | Ahluwalia |
| 9,011,412 B2 | 4/2015 | Albritton et al. |
| 9,089,631 B2 | 7/2015 | Schaeffer et al. |
| 9,095,646 B2 | 8/2015 | Chow et al. |
| 9,095,682 B2 | 8/2015 | Romoscanu |
| 9,119,926 B2 | 9/2015 | Cuevas et al. |
| 9,138,347 B2 | 9/2015 | Wiljanen et al. |
| 9,155,453 B2 | 10/2015 | Kumar et al. |
| 9,155,454 B2 | 10/2015 | Sahney et al. |
| 9,167,958 B2 | 10/2015 | Banik et al. |
| 9,179,968 B2 | 11/2015 | Leo et al. |
| 9,186,044 B2 | 11/2015 | Kucklick et al. |
| 9,186,055 B2 | 11/2015 | Kucklick |
| 9,192,284 B2 | 11/2015 | Hirsch et al. |
| 9,204,786 B2 | 12/2015 | Kucklick |
| 9,241,612 B2 | 1/2016 | Hoshino |
| 9,248,228 B2 | 2/2016 | Bono et al. |
| 9,339,631 B2 | 5/2016 | Graham et al. |
| 9,358,061 B2 | 6/2016 | Plascencia et al. |
| 9,360,124 B2 | 6/2016 | Schaeffer et al. |
| 9,387,121 B2 | 7/2016 | Wiljanen et al. |
| 9,427,504 B2 | 8/2016 | Newman |
| 9,545,334 B2 | 1/2017 | Steen et al. |
| 9,572,933 B2 | 2/2017 | Grannell et al. |
| 9,622,646 B2 | 4/2017 | Ouyang et al. |
| 9,668,643 B2 | 6/2017 | Kennedy et al. |
| 9,717,397 B2 | 8/2017 | Kucklick |
| 9,743,827 B2 | 8/2017 | Yasunaga et al. |
| 9,744,276 B2 | 8/2017 | Ahluwalia |
| 9,757,195 B2 | 9/2017 | Plascencia et al. |
| 9,775,674 B2 | 10/2017 | Schaeffer et al. |
| 9,810,836 B2 | 11/2017 | Okagami et al. |
| 9,814,490 B2 | 11/2017 | Neoh et al. |
| 9,820,762 B2 | 11/2017 | Cadeddu et al. |
| 9,827,009 B2 | 11/2017 | Kucklick et al. |
| 9,833,130 B2 | 12/2017 | Schaeffer et al. |
| 9,839,739 B2 | 12/2017 | Qian |
| 9,861,788 B2 | 1/2018 | Yu et al. |
| 9,878,145 B2 | 1/2018 | Holm et al. |
| 9,883,960 B2 | 2/2018 | Cummins et al. |
| 9,884,143 B2 | 2/2018 | Kobida et al. |
| 9,918,859 B2 | 3/2018 | Cummins et al. |
| 9,936,963 B2 | 4/2018 | Batchelor et al. |
| 9,968,249 B2 | 5/2018 | Huang et al. |
| 9,974,554 B2 | 5/2018 | Antonelli et al. |
| 9,980,631 B2 | 5/2018 | Schaeffer et al. |
| 9,982,791 B2 | 5/2018 | Schaeffer et al. |
| 10,004,385 B2 | 6/2018 | Bresco Torras et al. |
| 10,010,657 B2 | 7/2018 | Torrance et al. |
| 10,010,700 B2 | 7/2018 | Romoscanu |
| 10,028,763 B2 | 7/2018 | Kumar et al. |
| 10,076,432 B2 | 9/2018 | Cummins et al. |
| 10,085,624 B2 | 10/2018 | Isoda et al. |
| 10,092,173 B2 | 10/2018 | Dejima |
| 10,098,768 B2 | 10/2018 | Cummins et al. |
| 10,105,247 B2 | 10/2018 | Cummins et al. |
| 10,154,919 B2 | 12/2018 | Cummins et al. |
| 10,165,933 B2 | 1/2019 | Dejima |
| 10,166,013 B2 | 1/2019 | Nguyen et al. |
| 10,213,533 B2 | 2/2019 | Walter |
| 10,220,123 B2 | 3/2019 | Monty et al. |
| 10,231,793 B2 | 3/2019 | Romo |
| 10,244,927 B2 | 4/2019 | Kennedy, II et al. |
| 10,245,359 B2 | 4/2019 | Bono et al. |
| 10,251,539 B2 | 4/2019 | Sahney et al. |
| 10,251,671 B2 | 4/2019 | Dejima |
| 10,265,056 B2 | 4/2019 | Stanton et al. |
| 10,271,716 B2 | 4/2019 | Ferreira et al. |
| 10,286,141 B2 | 5/2019 | Monty et al. |
| 10,293,105 B2 | 5/2019 | Panotopoulos |
| 10,383,656 B2 | 8/2019 | Raulerson et al. |
| 10,434,259 B2 | 10/2019 | Dejima et al. |
| 10,441,134 B2 | 10/2019 | Ouyang et al. |
| 10,441,153 B2 | 10/2019 | Huang et al. |
| 10,441,460 B2 | 10/2019 | Ross et al. |
| 10,456,519 B2 | 10/2019 | Ngo-Chu et al. |
| 10,478,596 B2 | 11/2019 | Graham et al. |
| 10,492,662 B2 | 12/2019 | Govrin et al. |
| 10,500,323 B2 | 12/2019 | Huering et al. |
| 10,507,303 B2 | 12/2019 | Terwey |
| 10,531,883 B1 | 1/2020 | Deville et al. |
| 10,561,440 B2 | 2/2020 | Look et al. |
| 10,583,272 B2 | 3/2020 | Yu et al. |
| 10,595,715 B2 | 3/2020 | Dejima |
| 10,596,306 B2 | 3/2020 | Ahluwalia |
| 10,610,622 B2 | 4/2020 | Jeong |
| 10,624,708 B2 | 4/2020 | Hunter |
| 10,625,062 B2 | 4/2020 | Matlock et al. |
| 10,694,927 B2 | 6/2020 | Kucklick |
| 10,722,253 B2 | 7/2020 | Deville et al. |
| 10,722,620 B2 | 7/2020 | Chuang et al. |
| 10,758,385 B2 | 9/2020 | Cummins et al. |
| 10,765,449 B2 | 9/2020 | Dejima |
| 10,842,519 B2 | 11/2020 | Suh et al. |
| 10,850,013 B2 | 12/2020 | Hsu et al. |
| 10,888,349 B2 | 1/2021 | Pereira et al. |
| 10,905,446 B2 | 2/2021 | Chae |
| 10,912,873 B2 | 2/2021 | Nitzan et al. |
| 10,918,365 B2 | 2/2021 | Kirkemo |
| 10,925,666 B2 | 2/2021 | Plascencia et al. |
| 10,932,798 B2 | 3/2021 | Shelton et al. |
| 10,952,758 B1 | 3/2021 | Evans |
| 10,959,868 B2 | 3/2021 | Cummins et al. |
| 10,966,737 B2 | 4/2021 | Nguyen |
| 10,967,107 B2 | 4/2021 | Forsberg et al. |
| 10,980,554 B2 | 4/2021 | Sperry et al. |
| 11,013,522 B2 | 5/2021 | Ciulla |
| 11,026,715 B2 | 6/2021 | Mayberry |
| 11,035,481 B2 | 6/2021 | Schaeffer et al. |
| 11,051,678 B2 | 7/2021 | Nieman |
| 11,064,869 B2 | 7/2021 | McWeeney et al. |
| 11,064,871 B2 | 7/2021 | Gerbo et al. |
| 11,076,755 B2 | 8/2021 | Huang et al. |
| 11,089,944 B2 | 8/2021 | Rentschler et al. |
| 11,090,072 B2 | 8/2021 | Morey et al. |
| 11,096,555 B2 | 8/2021 | Harrah et al. |
| 11,096,568 B2 | 8/2021 | Harrah et al. |
| 11,109,874 B2 | 9/2021 | Gavala et al. |
| 11,116,530 B2 | 9/2021 | Yurek |
| 11,123,483 B2 | 9/2021 | Panotopoulos |
| 11,141,177 B2 | 10/2021 | Ganz et al. |
| 11,141,185 B2 | 10/2021 | Efremkin |
| 11,167,077 B2 | 11/2021 | Long et al. |
| 11,179,520 B2 | 11/2021 | Farah et al. |
| 11,185,380 B2 | 11/2021 | Burbank et al. |
| 11,241,243 B2 | 2/2022 | Pereira et al. |
| 11,241,290 B2 | 2/2022 | Waterbury et al. |
| 11,260,928 B2 | 3/2022 | Taylor |
| 11,278,300 B2 | 3/2022 | Bahmanyar et al. |
| 11,284,912 B2 | 3/2022 | St. George |
| 11,284,940 B2 | 3/2022 | Shelton |
| 11,324,526 B2 | 5/2022 | Yurek |
| 11,330,966 B2 | 5/2022 | Harrah et al. |
| 11,357,523 B2 | 6/2022 | Bionda et al. |
| 11,382,643 B2 | 7/2022 | Horowitz et al. |
| 11,382,650 B2 | 7/2022 | Noonan et al. |
| 11,382,652 B2 | 7/2022 | Wasdyke et al. |
| 11,382,693 B2 | 7/2022 | Harrah et al. |
| 11,399,892 B2 | 8/2022 | Yu et al. |
| 11,419,679 B2 | 8/2022 | Khachaturov et al. |
| 11,433,172 B2 | 9/2022 | Gao et al. |
| 11,452,436 B2 | 9/2022 | Chu et al. |
| 11,452,534 B2 | 9/2022 | Pereira et al. |
| 11,471,175 B2 | 10/2022 | Nguyen et al. |
| 11,471,176 B2 | 10/2022 | Greenhalgh et al. |
| 11,490,912 B2 | 11/2022 | Bonneau et al. |

(56) References Cited

U.S. PATENT DOCUMENTS

| | | |
|---|---|---|
| 11,490,913 B2 | 11/2022 | Nguyen et al. |
| 11,503,993 B2 | 11/2022 | Chu et al. |
| 11,510,691 B2 | 11/2022 | Nguyen et al. |
| 11,534,190 B2 | 12/2022 | Chu |
| 11,534,249 B2 | 12/2022 | Romo et al. |
| 11,547,479 B2 | 1/2023 | Shelton et al. |
| 11,559,360 B2 | 1/2023 | Romo |
| 11,571,229 B2 | 2/2023 | Shah |
| 11,576,692 B2 | 2/2023 | Gatineau et al. |
| 11,576,853 B2 | 2/2023 | Petkoska et al. |
| 11,577,056 B2 | 2/2023 | Rentschler et al. |
| 11,589,881 B2 | 2/2023 | Horowitz et al. |
| 11,596,423 B2 | 3/2023 | Nguyen et al. |
| 11,602,262 B2 | 3/2023 | Chu |
| 11,602,363 B2 | 3/2023 | Nguyen |
| 11,607,484 B2 | 3/2023 | Hanna et al. |
| 11,653,827 B2 | 5/2023 | Chu et al. |
| 11,672,598 B2 | 6/2023 | Morey et al. |
| 2003/0199986 A1 | 10/2003 | Mcweeney et al. |
| 2003/0216760 A1 | 11/2003 | Welch et al. |
| 2004/0019358 A1 | 1/2004 | Kear |
| 2004/0143197 A1 | 7/2004 | Soukup et al. |
| 2004/0153095 A1 | 8/2004 | Seddon |
| 2004/0153111 A1 | 8/2004 | Hosoada |
| 2004/0193103 A1 | 9/2004 | Kumar |
| 2004/0236312 A1 | 11/2004 | Nistal et al. |
| 2004/0267213 A1 | 12/2004 | Knapp |
| 2005/0085692 A1 | 4/2005 | Kiehn et al. |
| 2005/0085769 A1 | 4/2005 | MacMahon et al. |
| 2005/0143678 A1 | 6/2005 | Schwarz et al. |
| 2005/0149201 A1 | 7/2005 | Mcweeney et al. |
| 2006/0041186 A1 | 2/2006 | Vancaillie |
| 2006/0069343 A1 | 3/2006 | Rontal |
| 2006/0135948 A1 | 6/2006 | Vrma |
| 2006/0149127 A1 | 7/2006 | Seddiqui et al. |
| 2006/0206004 A1 | 9/2006 | Dehmel et al. |
| 2006/0264995 A1 | 11/2006 | Fanton et al. |
| 2007/0185383 A1 | 8/2007 | Mulhern et al. |
| 2007/0298069 A1 | 12/2007 | Bucay-couto et al. |
| 2008/0004578 A1 | 1/2008 | Nixon et al. |
| 2008/0058588 A1 | 3/2008 | Emanuel |
| 2008/0146991 A1 | 6/2008 | Hernandez et al. |
| 2008/0167526 A1 | 7/2008 | Crank et al. |
| 2008/0167527 A1 | 7/2008 | Slenker et al. |
| 2008/0249483 A1 | 10/2008 | Slenker et al. |
| 2009/0163846 A1 | 6/2009 | Aklog et al. |
| 2009/0270894 A1 | 10/2009 | Rubin et al. |
| 2010/0010431 A1 | 1/2010 | Tulley |
| 2010/0056867 A1 | 3/2010 | Labombard et al. |
| 2010/0137846 A1 | 6/2010 | Desai et al. |
| 2010/0305475 A1 | 12/2010 | Hinchliffe et al. |
| 2011/0004197 A1 | 1/2011 | Sansoucy |
| 2011/0060315 A1 | 3/2011 | Windheuser et al. |
| 2011/0202039 A1 | 8/2011 | Schaaf |
| 2011/0224489 A1 | 9/2011 | Deal et al. |
| 2011/0245841 A1 | 10/2011 | Shohat et al. |
| 2012/0041358 A1 | 2/2012 | Mann et al. |
| 2012/0220832 A1 | 8/2012 | Nakade et al. |
| 2013/0024003 A1 | 1/2013 | Mcweeney et al. |
| 2013/0123721 A1 | 5/2013 | Stiehl et al. |
| 2013/0131445 A1 | 5/2013 | Zerfas et al. |
| 2013/0138036 A1 | 5/2013 | Solomon et al. |
| 2013/0165944 A1 | 6/2013 | Gal et al. |
| 2013/0231605 A1 | 9/2013 | Walter |
| 2013/0253387 A1 | 9/2013 | Bonutti et al. |
| 2014/0107565 A1 | 4/2014 | Wiljanen et al. |
| 2014/0171922 A1 | 6/2014 | Douglas et al. |
| 2014/0180010 A1 | 6/2014 | Kumar et al. |
| 2014/0207056 A1 | 7/2014 | Bono et al. |
| 2014/0276207 A1 | 9/2014 | Ouyang et al. |
| 2014/0276377 A1 | 9/2014 | Chang et al. |
| 2014/0288460 A1 | 9/2014 | Ouyang et al. |
| 2014/0296868 A1 | 10/2014 | Garrison et al. |
| 2014/0296894 A1 | 10/2014 | Kojima et al. |
| 2015/0038785 A1 | 2/2015 | Govrin et al. |
| 2015/0141907 A1 | 5/2015 | Clement et al. |
| 2015/0150441 A1 | 6/2015 | Ouyang et al. |
| 2015/0164595 A1 | 6/2015 | Bogusky et al. |
| 2015/0305759 A1 | 10/2015 | St. George et al. |
| 2015/0328394 A1 | 11/2015 | Chow et al. |
| 2016/0001050 A1 | 1/2016 | Yee et al. |
| 2016/0022289 A1 | 1/2016 | Wan |
| 2016/0030070 A1 | 2/2016 | Eisner |
| 2016/0120557 A1 | 5/2016 | Goddard et al. |
| 2016/0270804 A1 | 9/2016 | Honda et al. |
| 2016/0374710 A1 | 12/2016 | Sinelnikov et al. |
| 2016/0374755 A1 | 12/2016 | Mirigian et al. |
| 2017/0027604 A1 | 2/2017 | Wallace |
| 2017/0065752 A1 | 3/2017 | Eisner |
| 2017/0215897 A1 | 8/2017 | Fan |
| 2017/0215899 A1 | 8/2017 | Harrah et al. |
| 2017/0215964 A1 | 8/2017 | Harrah et al. |
| 2017/0215965 A1 | 8/2017 | Harrah et al. |
| 2017/0252051 A1 | 9/2017 | Wan et al. |
| 2017/0252103 A1 | 9/2017 | Griefeneder et al. |
| 2017/0258550 A1* | 9/2017 | Vazales ................ A61B 90/70 |
| 2017/0266046 A1 | 9/2017 | Steen et al. |
| 2017/0303940 A1 | 10/2017 | Sperry et al. |
| 2017/0303941 A1 | 10/2017 | Eisner |
| 2017/0319776 A1 | 11/2017 | Eisner |
| 2017/0333614 A1 | 11/2017 | Gao et al. |
| 2017/0340862 A1 | 11/2017 | Calabrese et al. |
| 2017/0354431 A1 | 12/2017 | Rubin et al. |
| 2018/0055568 A1 | 3/2018 | Shelton et al. |
| 2018/0206866 A1 | 7/2018 | Wan |
| 2018/0360480 A1 | 12/2018 | Ciulla |
| 2019/0038817 A1 | 2/2019 | Forsberg et al. |
| 2019/0059988 A1 | 2/2019 | Davison et al. |
| 2019/0099209 A1 | 4/2019 | Witt et al. |
| 2019/0192222 A1 | 6/2019 | Mirigian et al. |
| 2019/0274699 A1 | 9/2019 | Morey et al. |
| 2019/0290811 A1 | 9/2019 | Bono et al. |
| 2019/0314044 A1 | 10/2019 | Long et al. |
| 2019/0328412 A1 | 10/2019 | Mazhar et al. |
| 2019/0343586 A1 | 11/2019 | Bonneau et al. |
| 2019/0357762 A1 | 11/2019 | Clayman et al. |
| 2020/0009302 A1 | 1/2020 | Pyle |
| 2020/0046393 A1 | 2/2020 | Kendale et al. |
| 2020/0069319 A1 | 3/2020 | Harrah et al. |
| 2020/0147294 A1 | 5/2020 | Edwards |
| 2020/0178767 A1 | 6/2020 | Miller |
| 2020/0178773 A1 | 6/2020 | Miller |
| 2020/0188014 A1 | 6/2020 | Woloszko et al. |
| 2020/0196843 A1 | 6/2020 | Tah et al. |
| 2020/0229907 A1 | 7/2020 | Duehlmeier |
| 2020/0297362 A1 | 9/2020 | Deville et al. |
| 2020/0397507 A1 | 12/2020 | Liu |
| 2020/0397975 A1 | 12/2020 | Kirk et al. |
| 2021/0015507 A1 | 1/2021 | Roberts et al. |
| 2021/0015509 A1 | 1/2021 | Wan |
| 2021/0022756 A1 | 1/2021 | Ciulla |
| 2021/0022757 A1 | 1/2021 | Wan |
| 2021/0022759 A1 | 1/2021 | Wan |
| 2021/0076904 A1 | 3/2021 | Calabrese et al. |
| 2021/0084766 A1 | 3/2021 | Govrin |
| 2021/0085158 A1 | 3/2021 | Ikuma et al. |
| 2021/0093338 A1 | 4/2021 | Baker et al. |
| 2021/0093340 A1 | 4/2021 | Baker et al. |
| 2021/0093341 A1 | 4/2021 | Baker et al. |
| 2021/0113268 A1 | 4/2021 | Waisman et al. |
| 2021/0121188 A1 | 4/2021 | Yurek |
| 2021/0177444 A1 | 6/2021 | Shelton et al. |
| 2021/0178032 A1 | 6/2021 | Hsu et al. |
| 2021/0228274 A1 | 7/2021 | Pyro et al. |
| 2021/0236204 A1 | 8/2021 | Tower et al. |
| 2021/0275248 A1 | 9/2021 | Pyro et al. |
| 2021/0307589 A1 | 10/2021 | Rentschler et al. |
| 2021/0315595 A1 | 10/2021 | Crawford et al. |
| 2021/0315608 A1 | 10/2021 | Mozloom, Jr. |
| 2021/0321861 A1 | 10/2021 | McWeeney et al. |
| 2021/0322040 A1 | 10/2021 | Gavala et al. |
| 2021/0330309 A1 | 10/2021 | Ma et al. |
| 2021/0338064 A1 | 11/2021 | Fitterer et al. |
| 2021/0338257 A1 | 11/2021 | Morey et al. |

(56) References Cited

U.S. PATENT DOCUMENTS

| | | |
|---|---|---|
| 2021/0361356 A1 | 11/2021 | Shelton et al. |
| 2021/0369095 A1 | 12/2021 | Stem et al. |
| 2021/0378740 A1 | 12/2021 | Chu et al. |
| 2021/0386273 A1 | 12/2021 | Purohit et al. |
| 2022/0000508 A1 | 1/2022 | Schmitt et al. |
| 2022/0022912 A1 | 1/2022 | Efremkin et al. |
| 2022/0023528 A1 | 1/2022 | Long et al. |
| 2022/0023563 A1 | 1/2022 | Ganz et al. |
| 2022/0031392 A1 | 2/2022 | Maher et al. |
| 2022/0047283 A1 | 2/2022 | Baker et al. |
| 2022/0047287 A1 | 2/2022 | Stender et al. |
| 2022/0047332 A1 | 2/2022 | Schmitt et al. |
| 2022/0053995 A1 | 2/2022 | Knollman et al. |
| 2022/0053998 A1 | 2/2022 | Ghani et al. |
| 2022/0054162 A1 | 2/2022 | Efremkin |
| 2022/0061827 A1 | 3/2022 | Schmitt et al. |
| 2022/0061866 A1 | 3/2022 | Crawford et al. |
| 2022/0072213 A1 | 3/2022 | Thoreson |
| 2022/0087697 A1 | 3/2022 | Yurek |
| 2022/0087698 A1 | 3/2022 | Yurek |
| 2022/0096108 A1 | 3/2022 | Baker et al. |
| 2022/0104839 A1 | 4/2022 | Horowitz et al. |
| 2022/0104840 A1 | 4/2022 | Horowitz et al. |
| 2022/0133340 A1 | 5/2022 | Schaeffer et al. |
| 2022/0135171 A1 | 5/2022 | Taylor |
| 2022/0142463 A1 | 5/2022 | Altshuler et al. |
| 2022/0142659 A1 | 5/2022 | Melsheimer et al. |
| 2022/0168003 A1 | 6/2022 | Crowley |
| 2022/0183706 A1 | 6/2022 | Pereira et al. |
| 2022/0202285 A1 | 6/2022 | Bukesov et al. |
| 2022/0226016 A1 | 6/2022 | Ganz et al. |
| 2022/0218367 A1 | 7/2022 | Ghani et al. |
| 2022/0218416 A1 | 7/2022 | Vogel |
| 2022/0233199 A1 | 7/2022 | Du et al. |
| 2022/0240761 A1 | 8/2022 | Harrah et al. |
| 2022/0240762 A1 | 8/2022 | Rentschler et al. |
| 2022/0265350 A1 | 8/2022 | Clayman et al. |
| 2022/0273860 A1 | 9/2022 | Wiener et al. |
| 2022/0280021 A1 | 9/2022 | Chu |
| 2022/0287774 A1 | 9/2022 | Ikuma et al. |
| 2022/0287775 A1 | 9/2022 | Harrah et al. |
| 2022/0296300 A1 | 9/2022 | Takata |
| 2022/0304548 A1 | 9/2022 | Chu |
| 2022/0313290 A1 | 10/2022 | Obermiller et al. |
| 2022/0323153 A1 | 10/2022 | Yu et al. |
| 2022/0338891 A1 | 10/2022 | Johnson et al. |
| 2022/0354520 A1 | 11/2022 | Mannion et al. |
| 2022/0362449 A1 | 11/2022 | Gao et al. |
| 2022/0362511 A1 | 11/2022 | Gavalis et al. |
| 2022/0369906 A1 | 11/2022 | Wilson et al. |
| 2022/0369919 A1 | 11/2022 | Chu et al. |
| 2022/0370085 A1 | 11/2022 | Reagan, Jr. et al. |
| 2022/0370127 A1 | 11/2022 | Khachaturov et al. |
| 2022/0386852 A1 | 12/2022 | Chu et al. |
| 2022/0387534 A1 | 12/2022 | Petkoska |
| 2022/0401119 A1 | 12/2022 | Pereira et al. |
| 2023/0028334 A1 | 1/2023 | Aljure |
| 2023/0030708 A1 | 2/2023 | Noonan et al. |
| 2023/0031136 A1 | 2/2023 | Ikuma |
| 2023/0055911 A1 | 2/2023 | Chu et al. |
| 2023/0063701 A1 | 3/2023 | Horowitz et al. |
| 2023/0066304 A1 | 3/2023 | Nguyen et al. |
| 2023/0075988 A1 | 3/2023 | Scheib et al. |
| 2023/0081712 A1 | 3/2023 | Shelton et al. |
| 2023/0083127 A1 | 3/2023 | Hayashi et al. |
| 2023/0103647 A1 | 4/2023 | Nguyen et al. |
| 2023/0113437 A1 | 4/2023 | Horie et al. |
| 2023/0113650 A1 | 4/2023 | Sasaguchi |
| 2023/0115997 A1 | 4/2023 | Sato et al. |
| 2023/0125143 A1 | 4/2023 | Schmitt |
| 2023/0130679 A1 | 4/2023 | Avolos |
| 2023/0130759 A1 | 4/2023 | Shelton |
| 2023/0131637 A1 | 4/2023 | Shelton et al. |
| 2023/0145569 A1 | 5/2023 | McWeeney et al. |
| 2023/0146163 A1 | 5/2023 | Yurek |
| 2023/0146598 A1 | 5/2023 | Yurek |
| 2023/0148845 A1 | 5/2023 | McWeeney et al. |
| 2023/0165599 A1 | 6/2023 | Nguyen et al. |
| 2023/0181011 A1 | 6/2023 | Chu |
| 2023/0181203 A1 | 6/2023 | Nguyen et al. |
| 2023/0181204 A1 | 6/2023 | Shah |
| 2023/0190078 A1 | 6/2023 | Clayman et al. |
| 2023/0190316 A1 | 6/2023 | Nguyen |
| 2023/0190317 A1 | 6/2023 | Horowitz et al. |
| 2023/0190373 A1 | 6/2023 | Hutchens et al. |
| 2023/0210586 A1 | 7/2023 | Mantri et al. |
| 2023/0263369 A1 | 8/2023 | Chu et al. |
| 2023/0263571 A1 | 8/2023 | Chu et al. |
| 2023/0301718 A1 | 9/2023 | Harrah et al. |
| 2023/0346202 A1 | 11/2023 | Harrah et al. |
| 2024/0057855 A1 | 2/2024 | Reed et al. |
| 2024/0099563 A1 | 3/2024 | Wales et al. |
| 2024/0130743 A1 | 4/2024 | Hajjar |
| 2024/0138666 A1 | 5/2024 | Chu et al. |
| 2024/0138913 A1 | 5/2024 | Carlson et al. |
| 2024/0148394 A1 | 5/2024 | Baker et al. |

FOREIGN PATENT DOCUMENTS

| | | |
|---|---|---|
| CN | 203988361 U | 12/2014 |
| KR | 10-2167406 B1 | 10/2020 |
| WO | WO 2010/068467 A1 | 6/2010 |
| WO | WO 2014/160201 A1 | 10/2014 |
| WO | WO 2017/135980 A1 | 8/2017 |
| WO | WO 2018/215954 A1 | 11/2018 |
| WO | WO 2019/178387 A1 | 9/2019 |
| WO | WO 2020/146454 A1 | 7/2020 |
| WO | WO 2020/150713 A2 | 7/2020 |
| WO | WO 2020/247103 A1 | 12/2020 |

OTHER PUBLICATIONS

Chen, et al: "The Comparison Study of Flexible Ureteroscopic Suctioning Lithotripsy With Intelligent Pressure Control Versus Minimally Invasive Percutaneous Suctioning Nephrolithotomy in Treating Renal Calculi of 2 to 3 cm in Size", Surgical Innovation 2019; vol. 26(5); pp. 528-535, 8 pages.

Chew, et al., "Natural History, Complications and Re-Intervention Rates of Asymptomatic Residual Stone Fragments after Ureteroscopy: a Report from the EDGE Research Consortium", The Journal of Urology; Apr. 2016 (published online Nov. 2015); vol. 195, pp. 982-986.

Communication dated Oct. 26, 2021 forwarding the extended European Search Report for European Patent Application No. 19746731.9; 12 pages.

Deng, et al., "A Novel Flexible Ureteroscopy with Intelligent Control of Renal Pelvic Pressure: An Initial Experience of 93 Cases", Journal of Endourology; Oct. 2016 (published online Aug. 2016); vol. 30(10), pp. 1067-1072, 6 pages.

Deng, et al., "Suctioning flexible ureteroscopy with automatic controlof renal pelvic pressure: a porcine model", International Journal of Clinical and Experimental Medicine, Mar. 30, 2016, 6 pages.

Emmott, et al., "Complications, Re-Intervention Rates, and Natural History of Residual Stone Fragments After Percutaneous Nephrolithotomy", Journal of Endourology; Jan. 2018; vol. 32(1), pp. 28-32.

Final Office Action dated Aug. 25, 2023, for U.S. Appl. No. 18/090,802, 29 pages.

Huang, et al., "Endourology and Stones | The Application of Suctioning Flexible Ureteroscopy With Intelligent Pressure Control in Treating Upper Urinary Tract Calculi on Patients With a Solitary Kidney", Urology Jan. 2018; vol. 111, pp. 44-47.

International Search Report and Written Opinion mailed Jul. 31, 2023 for International Patent Application No. PCT/US2023/014276, 60 pages.

Invitation To Pay Additional Fees And, Where Applicable, Protest Fee mailed May 24, 2023 for International Patent Application No. PCT/US2023/014276; 14 pages.

(56) References Cited

OTHER PUBLICATIONS

Jiang, et al: "Ex Vivo Renal Stone Dusting: Impact of Laser Modality, Ureteral Access Sheath, and Suction on Total Stone Clearance", Journal of Endourology; Apr. 2022; vol. 36(4); pp. 499-507.
Karani, et al: "Evaluation of a Novel Female Gender Flexible Ureteroscope: Comparison of Flow and Deflection to a Standard Flexible Ureteroscope", Journal of Endourology; Jun. 2021; vol. 35(6); pp. 840-846.
Keller, et al: "Next-Generation Fiberoptic and Digital Ureteroscopes", Urol Clin North Am.; May 2019; vol. 46(2); pp. 147-163.
Kim, et al., "The Clinical Efficacy of Dual-Lumen Catheter Technique in Retrograde Intrarenal Surgery for the Management of Nephrolithiasis: A Propensity Score Analysis", Journal of Endourology; Dec. 2018; vol. 32(12).
Lai, et al: "RIRS with Vacuum-Assisted Ureteral Access Sheath versus MPCNL for the Treatment of 2-4cm Renal Stone", BioMed Research International 2020; vol. 2020, Article ID 8052013, 8 pages.
Leveillee, et al., "Impressive Performance: New Disposable Digital Ureteroscope Allows for Extreme Lower Pole Access and Use of 365 um Holmium Laser Fiber", Journal of Endourology Case Reports; Jun. 1, 2016; vol. 2(1), pp. 114-116.
Li, et al., "A Novel Semirigid Ureterorenoscope with Vacuum Suctioning System for Management of Single Proximal Ureteral and Renal Pelvic Stones: An Initial Experience", Journal of Endourology; Dec. 2018; vol. 32(12), pp. 1154-1159, 6 pages.
Non-Final Office Action dated Apr. 28, 2023 for U.S. Appl. No. 18/090,802, 29 pages.
Non-final office action mailed Aug. 9, 2023 for U.S. Appl. No. 16/966,856, 40 pages.
Non-final office action mailed Aug. 9, 2023 for U.S. Appl. No. 17/489,723; 25 pages.
Non-final office action mailed Aug. 9, 2023 for U.S. Appl. No. 18/091,308; 27 pages.
Non-final office action mailed Jan. 21, 2022 for U.S. Appl. No. 17/489,733, 6 pages.
Peng, et al., "Suctioning flexible ureteroscopic lithotripsy in the oblique supine lithotomy position and supine lithotomy position: a comparative retrospective study", Minerva Urologica e Nefrologica, Dec. 2018; vol. 70(6), pp. 612-616.
Portis, et al., "Endourology and Stones | Repeat Surgery After Ureteroscopic Laser Lithotripsy With Attempted Complete Extraction of Fragments: Long-term Follow-up", Urology Jun. 2015; vol. 85(6), pp. 1272-1278.
Raman, et al., "Natural History of Residual Fragments Following Percutaneous Nephrostolithotomy", Journal of Urology Mar. 2009; vol. 181(3), pp. 1163-1168.
Rebuck, et al., "Endourology and Stones | The Natural History of Renal Stone Fragments Following Ureteroscopy", Urology Mar. 2011; vol. 77(3), pp. 564-568.
Scales, et al., "The impact of unplanned postprocedure visits in the management of patients with urinary stones", Surgery May 2014; vol. 155(5), pp. 769-775.
Schneider, et al: "In Vitro Evaluation of Stone Fragment Evacuation by Suction", Journal of Endourology; Feb. 2021; vol. 35(2); pp. 187-191.
Skolarikos, et al., "Urolithiasis/Endourology | Outcomes of Flexible Ureterorenoscopy for Solitary Renal Stones in the CROES URS Global Study", Journal of Urology Jul. 2015; vol. 194(1), pp. 137-143.
Villanueva, et al., "Silicone Catheters May Be Superior to Latex Catheters in Difficult Urethral Catheterization After Urethral Dilation", Journal of Endourology 2011, vol. 25(5), pp. 841-844.
Williams, et al: "A lumped-parameter model for kidney pressure during stone removal," IMA Journal of Applied Mathematics; Oct. 2020; vol. 85(5); pp. 703-723.
Williams, et al: "The Fluid Mechanics of Ureteroscope Irrigation", Journal of Endourology; Jan. 2019; vol. 33(1); pp. 28-34.
Williams, et al: "Cavity Flow Characteristics and Applications to Kidney Stone Removal," Journal of Fluid Mechanics 2020; vol. 902; A16.
Williams, et al: "Effects of Geometry on Resistance in Elliptical Pipe Flows," Journal of Fluid Mechanics 2020; vol. 891; A4-1.
Williams, et al: "Shape optimisation for faster washout in recirculating flows," Journal of Fluid Mechanics 2021; vol. 914; A37.
Zanetti, et al: "Vacuum-assisted mini-percutaneous nephrolithotomy: a new perspective in fragments clearance and intrarenal pressure control", World Journal of Urology 2021; vol. 39; pp. 1717-1723.
Zeng, et al., "Modified Access Sheath for Continuous Flow Ureteroscopic Lithotripsy: A Preliminary Report of a Novel Concept and Technique", Journal of Endourology Sep. 2016; vol. 30(9), pp. 992-996.

* cited by examiner

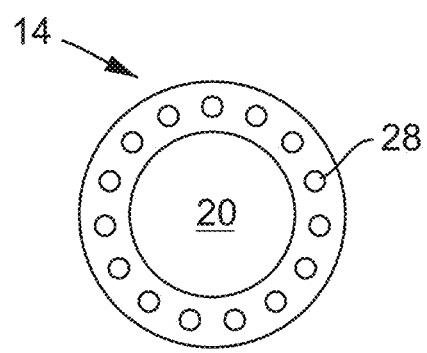 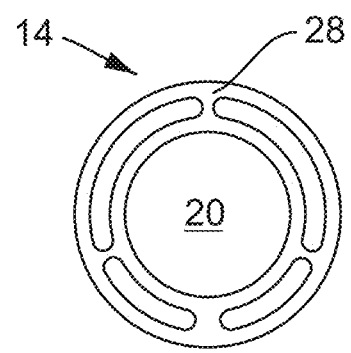
FIG. 2C
(Prior Art)
FIG. 2D
(Prior Art)

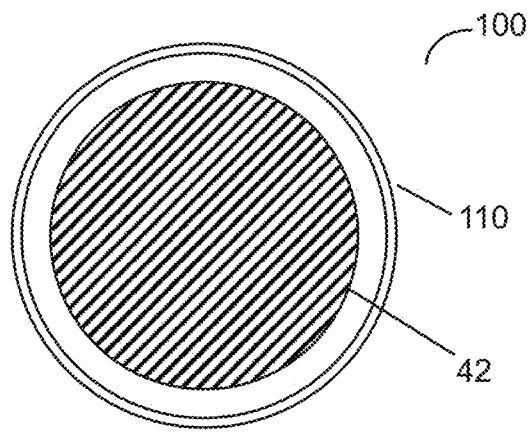
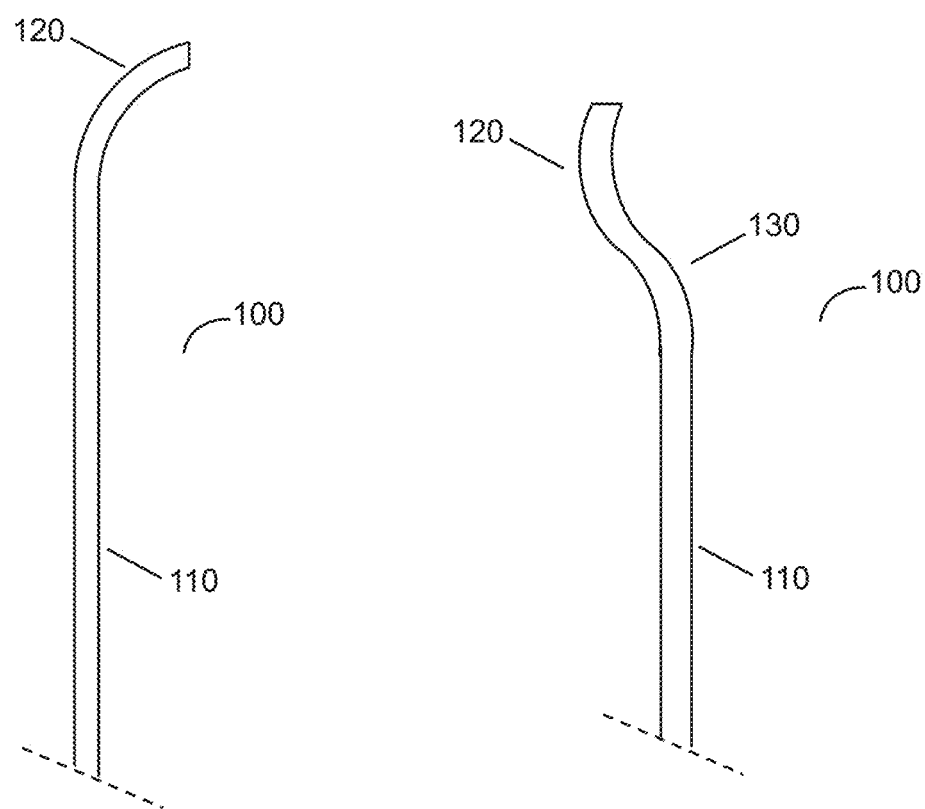
FIG. 11A
FIG. 11B
FIG. 11C

TOOL GUIDING DEVICE FOR KIDNEY STONE TREATMENT APPARATUS

This application is a continuation of application Ser. No. 18/373,229, filed Sep. 26, 2023, which in turn claims priority to, and the benefit of, U.S. Provisional Patent Application No. 63/411,568, filed Sep. 29, 2022, the contents of all of which are herein incorporated by reference in their entirety for all purposes.

FIELD

The present inventions are generally related to mechanisms for guiding a tool within a lumen of a medical device used to remove objects from the body. More particularly, the inventions are directed to a tool for guiding laser lithotripsy devices in kidney stone treatment catheters.

BACKGROUND

Kidney stones are a common medical problem that negatively affect millions of individuals worldwide. Kidney stones include one or more solid masses of material that are usually made of crystals and form in parts of the urinary tract including in the ureter, the kidney, and/or the bladder. Kidney stones range in size from small (less than about 1 cm) to very large (more than 4 cm) and may cause significant pain to the patient and damage to the kidney. One method of treatment for removal of kidney stones includes the use of an ureteroscope and an extraction catheter. A physician advances the ureteroscope through the ureter and into the kidney. The physician inspects the kidney with the ureteroscope, locating and counting the stones within the calyces of the kidney. A laser lithotripsy device is then inserted through the ureteroscope and is used to fragmentize the larger kidney stones into smaller pieces. The ureteroscope is then removed and an extraction catheter is introduced for removal of the fragmented and smaller, un-fragmented stones. The extraction catheter includes a vacuum lumen for removal of the stones through an aspiration port. The vacuum lumen is large in diameter to allow for the passage of the stones.

One problem associated with the above procedure is that the physician may have to repeat the insertion and removal of the ureteroscope and the extraction catheter to remove all of the stones. For example, a remaining fragmented stone could be too large for extraction by the catheter, which would necessitate reinsertion of the laser via the ureteroscope to fragmentize the stone. It is apparent that repeating the steps of reinsertion of the ureteroscope and extraction catheter increases the risk of complications to the patient, including tissue irritation and laceration. Accordingly, engineers have developed more advanced systems where the various components of the ureteroscope and extraction catheter are combined into one medical device. That is, catheter advancements have provided the ability to combine the camera, laser, aspiration, and irrigation components into one system, to streamline kidney stone removal procedure and reduce the chances of adverse consequences associated with this procedure.

A challenge associated with these advanced catheter systems has been the inability to maintain a suitable catheter diameter. The consolidation of components, especially a laser, requires additional channels, which would make the catheter larger in profile than desired. Larger diameter catheters can cause more tissue irritation and injury when navigated thought the ureter, renal pelvis, and renal calyces. In some instances, a large diameter catheter may not be able to access the kidney at all because of a narrow and/or tortuous ureter. One proposed solution for maintaining a low catheter profile has been the use existing lumens, such as the vacuum lumen, for the laser. The use of the vacuum lumen is plausible because it is wide enough to accommodate a laser. Laser fibers have diameters smaller than vacuum lumens (the diameter of the vacuum lumen is much larger than the diameter of the working channel of the ureteroscope that receives the laser device). However, this significant difference in diameter causes the laser fiber to move within the vacuum lumen. Unwanted movement of the laser fiber prevents the clinician from being able to target stones with precision. Any side-to-side movement of the laser fiber in the vacuum lumen not only makes it difficult to fragmentize the stones, but also can increase the risk of the laser causing damage to nearby tissues.

The embodiments of the present inventions provide a tool for allowing, inter alia, a laser to be effectively used with an extraction catheter system for fragmenting kidney stones while concomitantly allowing stones to flow past the laser and through the vacuum lumen.

SUMMARY

In accordance with one aspect of the inventions, a catheter assembly is provided comprising a working lumen and a guide. The guide is configured to position a fragmentizing device within the working lumen. The guide is configured to prevent or minimize any unintended movement of a distal section of the fragmentizing device within the working lumen when the distal section of the fragmentizing device is positioned at a distal end of the working lumen. In one embodiment, the working lumen is a vacuum lumen, and the guide is configured to be positioned in the vacuum lumen. The guide allows for fluid and debris to flow past the fragmentizing device and through the vacuum lumen for removal of fluid and debris. In one embodiment, the catheter assembly additionally comprises an actuating device for moving the guide in a back-and-forth direction within the vacuum lumen. The fragmentizing device can include a laser fiber or device.

The guide can comprise:
(a) a tubular body having a lumen configured to receive the fragmentizing device and wings extending from a distal end segment of the tubular body for creating flow gaps between the tubular body and an inner side of the working lumen;
(b) an elongated tube having a distal portion comprising one or more curved or bent sections that bias the distal portion of the elongated tube against an inner side of the working lumen;
(c) an elongated tube having a distal portion, wherein the distal portion has a cross-sectional perimeter that is not symmetric about a central longitudinal axis of the elongated tube;
(d) an elongated tube having a D-shaped, C-shaped, or U-shaped distal portion including a channel extending along the distal portion to accommodate the fragmentizing device;
(e) a first mechanical feature that is configured to mechanically engage with a second mechanical feature on an inner side of the working lumen;
(f) a magnetic feature that is configured to magnetically engage with a counterpart magnetic feature associated with the working lumen;
(g) a ring that is configured to be placed around the distal section of the fragmentizing device;

(h) a snare that is configured to receive the distal section of the fragmentizing device and to secure the distal section of fragmentizing device by constricting a loop of the snare; or (i) expandable elements located on an inner side of the working lumen, such that the expansion of the elements secures the distal section of the fragmentizing device.

In accordance with one aspect of the inventions, a kidney stone removal system is provided, comprising a vacuum tube and a laser guide configured to be removably inserted into the vacuum tube. The laser guide comprises a tubular body having a lumen configured to receive a laser device, and wings extending from a distal end segment of the tubular body for guiding the distal end segment of the tubular body in the vacuum tube and creating flow gaps between the tubular body and the vacuum tube.

In one embodiment, the tubular body is configured to not extend out of a distal end of the vacuum tube when the tubular body is inserted completely into the vacuum tube and placed in an operational position. In one embodiment, the guide comprises two to four wings. In one embodiment, the guide consists of three or four wings and a circumferential distance is the same between each pair of neighboring wings. In one embodiment, the guide consists of three or four wings and the circumferential distance between a first pair of the neighboring wings is different from a circumferential distance between a second pair of neighboring wings. The first pair and second pair of neighboring wings can share a common wing. In some embodiments, at least two of the gaps have different sizes.

In one embodiment, each wing comprises a middle segment having a rectangular shape, which transitions into tapered end segments that slope downward into the tubular body. In some embodiments, each wing has a variable thickness that increases from a proximal end of the wing to a distal end of the wing along a longitudinal axis. In some embodiments, each wing has a longitudinal axis that is at an angle relative to a longitudinal axis of the tubular body.

In accordance with another aspect of the inventions, the kidney stone removal system additionally comprising an actuator for moving the tubular body within the vacuum tube. In one embodiment, the actuator comprises a biasing element and a shaft coupled to the tubular body, such that actuation of the biasing element causes the shaft to move the tubular body in a back-and-forth direction within the vacuum tube. In one embodiment, the shaft is configured to be removably coupled to a proximal end of the tubular body. In an alternative embodiment, the shaft is permanently attached to a proximal end of the tubular body.

In one embodiment, the biasing element comprises a band coupled to a distal section of the shaft. The actuator can additionally comprise a cylindrical housing coupled to the band and configured to receive the shaft, such that an inward compression and release of the band causes a part of the shaft to telescopically move into and out from the cylindrical housing. The actuator comprises a channel for receiving the laser device. The channel is configured to be in commutation with the lumen of the tubular body.

In accordance with another aspect of the inventions, a catheter assembly is provided comprising a vacuum tube and a guiding device configured to be removably positioned in the vacuum tube for receiving a debris fragmentizing device. The guiding device is configured to prevent an unintended movement of the fragmentizing device when the fragmentizing device is positioned at a distal end of the vacuum tube, while allowing fluid and debris to flow past the fragmentizing device and through the vacuum tube. The catheter system can additionally include an actuating device for moving the guiding device within the vacuum tube for clearance of debris. The fragmentizing device can be a laser fiber.

In accordance with another aspect of the invention, a method of kidney stone removal with the use of all of the embodiments of the present inventions is provided.

BRIEF DESCRIPTION OF THE DRAWINGS

The figures are not to scale.

FIGS. 2C and 2D schematically depict exemplary variations of FIG. 2b.

FIG. 11A is front-end view of an embodiment of a guide.

FIG. 11B is a partial side plan view of an embodiment of a guide

FIG. 11C is a partial side plan view of another embodiment of a guide.

DETAILED DESCRIPTION OF EXEMPLARY EMBODIMENTS

Figure 1:
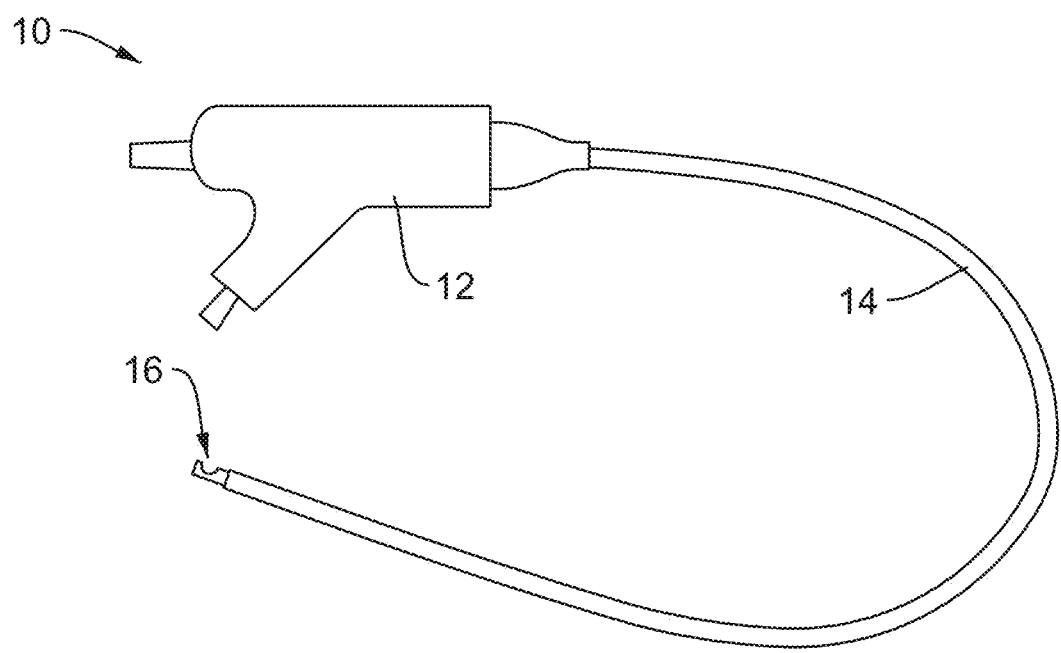
FIG. 1 is non-limiting example of a conventional catheter system.

FIG. 1 illustrates an exemplary system 10 used to remove debris, such as kidney stones. The system 10 includes a handle 12 from which a catheter 14 extends. The catheter 14 can include various ports and lumens, including vacuum, aspiration, and irrigation running along the length of the catheter 14. The system 10 can also include a camera (digital visualization and lighting, e.g., video chip and LED) positioned at an end, distal face of the catheter 14 for providing real time imaging to the physician. An aspiration port 16 is at the distal end of the catheter 14 for removal of the debris, with the assistance of the negative pressure applied through the vacuum lumen. While the aspiration port 16 is illustrated as being located on the side or lateral wall of the catheter, the aspiration port(s) can also be located on the end, distal face of the catheter 14. The handle 12 allows the physician to hold and operate the system 10. Handles commonly include features that allow a physical to operate various functions of the system, including the camera, vacuum pressure, the amount of irrigation and irrigation pressure, and the maneuverability of the catheter 14. For example, the handle 12 can include mechanical and electronic controls that allow the physician to adjust the amount of negative pressure, regulate the discharge of the irrigation fluid, and steer the catheter through tortuous anatomical passageways via the use of wheels and/or levers attached to cables, as is well known in the art.

Figure 2A:
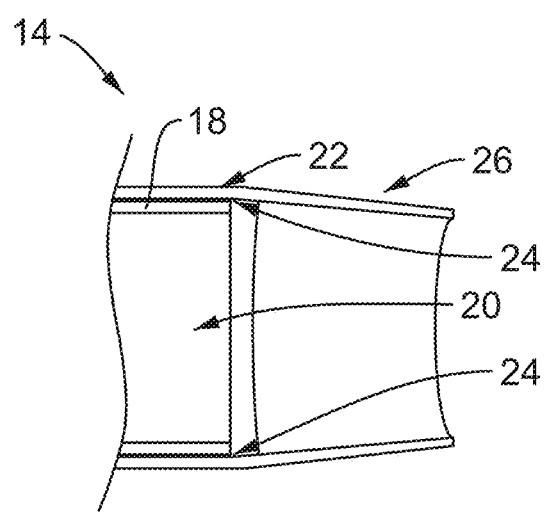
FIG. 2A schematically depicts a cross-section taken along the longitudinal axis of a distal end segment of the catheter system of FIG. 1.
Figure 2B:
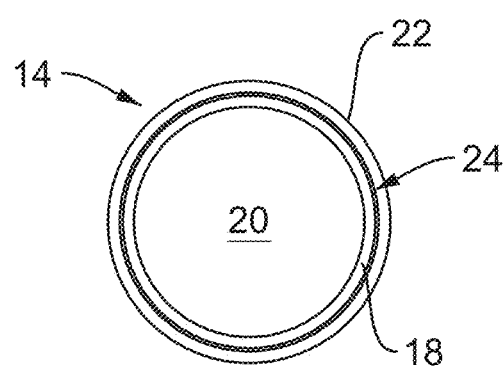
FIG. 2B schematically depicts a cross-section intersecting the longitudinal axis of FIG. 2A.

FIG. 2A schematically depicts a cross-section taken along the longitudinal axis of the distal end of the catheter system of FIG. 1. FIG. 2B schematically depicts a cross-section intersecting the longitudinal axis of FIG. 2A. The catheter 14 includes an inner tube 18 extending along the length of the catheter 14. The inner tube 18 forms a vacuum lumen 20 through which negative pressure is applied to extract debris, such as kidney stones. An outer tube 22 can circumscribe and be disposed over the inner tube 18. A space between the inner 18 and outer 22 tubes can define the irrigation channel 24. The physician can, therefore, supply an irrigation fluid, via the operation of the handle 12, through the channel 24 to irrigate the treatment area and tissues. The very distal end of the outer tube 22 can extend beyond the inner tube 18 to form a nozzle 26. The nozzle 26 can include a tapered shape to provide a nozzle outlet having a smaller diameter than an inlet segment of the nozzle 26. FIGS. 2C and 2D illustrate variations of FIG. 2B. The inner 18 and outer 22 tube can be configured to provide a plurality of separate channels 28, any one or a combination of which can be used for irrigation, aspiration, or other functions.

In accordance with one aspect of the present inventions, a vacuum lumen of the catheter can be used for insertion and retraction of stone fragmentation-inducing device such as a lithotripsy device or, most preferably, a laser lithotripsy device. An inner diameter of the inner tube 18 (i.e., the diameter of the vacuum lumen 20) needs to be large enough to accommodate passage of numerous stone fragments without clogging. In the embodiments of the present inventions, diameter of the vacuum lumen can be, for example, 2.0 mm to 3.0 mm, or in some configurations about 2.5 mm. Laser fibers and lithotripsy devices, however, have diameters considerably smaller than the vacuum lumen diameter. This significant difference in diameter causes the fragmentation-inducing device to move around or shift, during operation, within the vacuum lumen. The unintended movement of the laser makes it difficult for the physical to target stones with precision.

Figure 3:
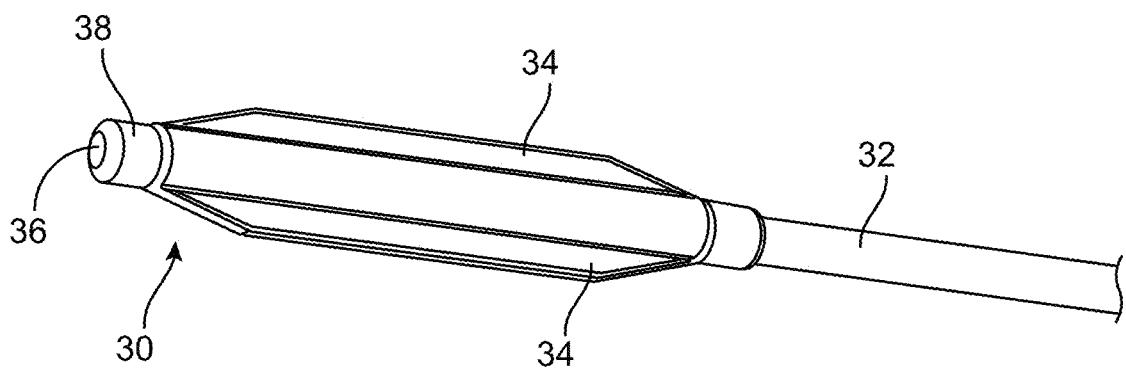
FIG. 3 is a partial perspective view of an embodiment of a guide.

Accordingly, the embodiments of the present inventions provide an intermediate device for securing the fragmentation-inducing device (preferably a laser device or fiber) into the vacuum lumen. The intermediate device is configured to completely prevent or significantly minimize the movement of the laser fiber at the distal end of the vacuum lumen, while not impeding the functionality of the vacuum lumen and allowing fluid and solids to flow past the laser fiber. FIG. 3 illustrates the intermediate device 30, referring to herein as a guide 30. The guide 30 includes an elongated body 32 that is configured to be inserted through a proximal end of a catheter (e.g., catheter 14) and pushed through the vacuum lumen (e.g., vacuum lumen 20) until a distal end of the guide 30 is positioned precisely at or approximately adjacent to the distal end of the vacuum lumen. In one embodiment, the length of the guide 30 is equivalent to length the vacuum lumen in which it is to be placed. Preferably, guide 30 is configured such that the distal tip of the guide 30 does not extend beyond the distal end opening of the vacuum lumen when the guide 30 is placed completely within the vacuum lumen or in operational position—that is, holding the laser tip at the distal end of the vacuum lumen. The guide 30 includes at least 2 wings, ridges, flanges, or extensions 34, terms which are used herein interchangeably. The wings 34 project or extend out from a distal segment of the elongated body 32. In one embodiment, the wings 34 extend from the distal segment of the elongate body 32 such that when the elongated body 32 is placed at its operational position within the vacuum lumen, the wings 34 reside at the distal most segment of the vacuum lumen. The wings 34 can be monolithic extensions of the elongated body 32—meaning, the body 32 and the wings are made from or molded from one piece. Alternatively, the wings 34 can be extensions of a smaller tube that is disposed over and attached to the distal segment of the elongated body 32. A lumen 36 extends though the center of the elongated body 32 for receiving the fragmentation-inducing device, preferably a laser fiber. The lumen 36 has a diameter for accommodating the laser fiber that is used. In other words, the dimeter of the lumen 36 is large enough to allow a laser fiber to be freely inserted therein and retracted therefrom, but small enough to prevent or significantly minimize any non-rotational or side-to-side movement of the laser fiber. The very distal end of the guide 30, in front of the wings 34, can include knob segment 38 having a tapered end of a smaller diameter than the elongated body 32. The knob segment 38 facilitates the insertion of the guide 30 into an access port of the vacuum lumen. The knob segment 38 can come into contact against a smaller tapered end of the vacuum lumen, such as the tapered nozzle 26, to prevent the guide 30 from extending out from the vacuum lumen.

Figure 4:
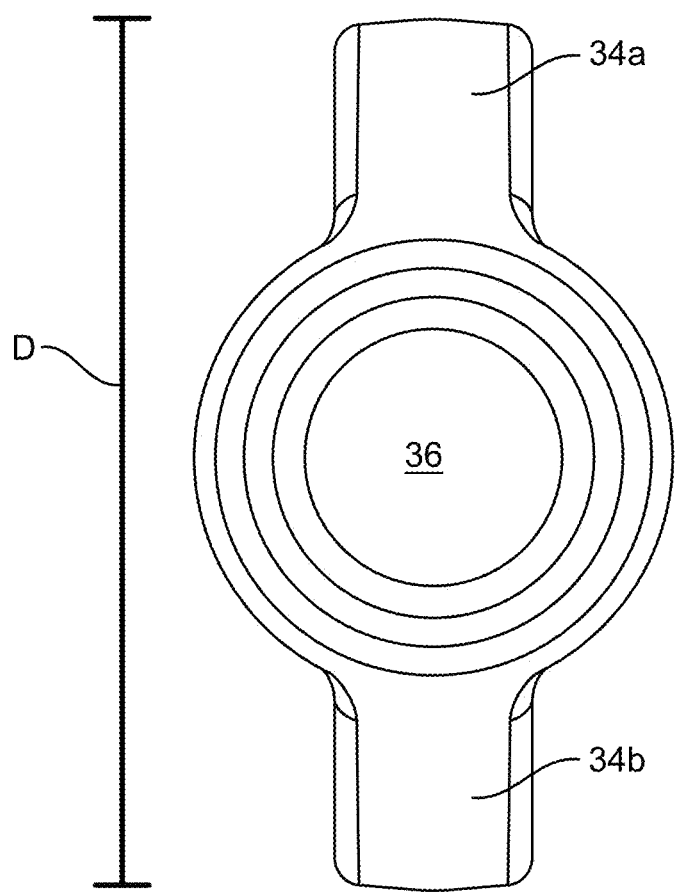
FIG. 4 is a front-end view of an embodiment of the guide.

FIG. 4 illustrates a front-end view of an embodiment of the guide 30. The guide includes (or consists of) two wings 34a and 34b extending from the elongated body 32. The wings 34a and 34b are sized to allow the guide 30 to freely glide into and out of the vacuum lumen, while preventing side-to-side or non-rotational movement of the winged-section of the guide 30 within the vacuum lumen. In other words, the greatest diameter D of the guide 30, which includes the width (i.e., height) of the wings 34, should be slightly smaller than the inner diameter of the vacuum lumen to allow the wings 34 to traverse through the vacuum lumen, yet prevent significant side-to-side movement of the wings 34 within the vacuum lumen. In one embodiment, the diameter D can match or be about equal to the inner diameter of the lumen. Here, the wings 34 can be made from a softer or more pliable plastic material that allows the wings 34 to slightly compress when fitted through the vacuum lumen.

While a preferred two-wing design is illustrated in FIG. 4, the guide 30 can include (or consist of) three wings 34 or four wings 34. While the embodiments of the inventions can include any number of wings, a 2 to 4 wing design is preferred because a greater number of wings can cause stones to clog the vacuum lumen or be lodged between the vacuum lumen and the elongated body 32, thus encumbering the functionality of the vacuum lumen.

Figure 5:
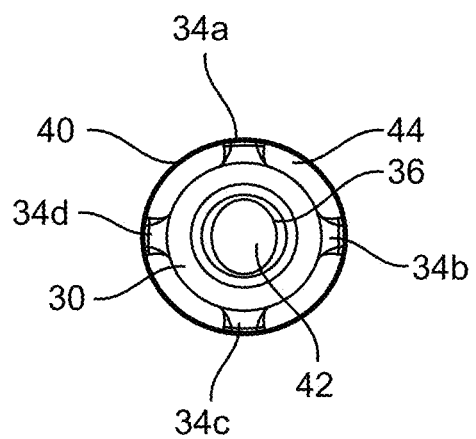
FIG. 5 is a schematic front-end view of an embodiment of the guide positioned inside of a vacuum tube.

FIG. 5 is a general schematic front-end view of the guide 30 comprising (or consisting of) four wings 34a-34d positioned at the distal most end of a vacuum tube 40 to secure a tip of a laser device or fiber at the distal tip of the vacuum tube 40. A laser device or fiber 42 is schematically shown positioned in the lumen 36 of the guide 30. The lumen's 36 restricted diameter, while allowing insertion and retraction of the laser fiber 42 through the guide 30, prevents or significantly minimizes movement of the laser fiber 42 within the vacuum tube 40 that is not intended by the physician. The stability of the laser 42 allows the physician to apply laser pulses to a kidney stone with great accurately, thus effectively fragmentizing the stones while reducing the risk of injury caused by deviated laser pulses. Wings 34a-34d should be of sufficient width or height (i.e., distance between the elongated body 32 and the vacuum tube 40) to create gaps 44 between the guide 30 and the vacuum tube 40. The gaps 44 allow the vacuum lumen to apply suction for removal of fluids, debris, and kidney stone fragments during the entire laser procedure. The number of wings 34 dictates the number of gaps 44. For example, two wings 34 provide two large gaps 44, three wings 35 provide three intermediate sized gaps 44, and the illustrated four-wing 34 configuration provides four smaller gaps 44. Larger gaps 44 are preferred to minimize the chances of stones becoming clogged or lodged at the entry point or along a distal section of the guide 30.

FIG. 5 shows four wings 34a-34d, where the circumferential distance is the same between any two neighboring wings. That is, the distance between each of 34a-35b, 34b-34c, 34c-34d, and 34d-34a is equal. In one embodiment, the circumferential distance between two neighboring wings can be different from the distance of another pair of neighboring wings (even if there is one shared wing). For example, the distance between neighboring wings 34a-34b and 34c-34d can be the same and the distance between 34a-34d and 34b-34c can be the same, but the distance between 34a-34b or 34d-34c is less than the distance between 34a-34d or 34b-34c. This configuration provides two small gaps 44 to allow passage of smaller stones and two large gaps 44 to allow passage of larger stones that may not have been able to be removed if the gaps 44 where the same size. In a three-wing configuration, the distance between each wing can vary, thus provided three gaps 44 each having a different size. Alternatively, in a three-wing configuration, the distance between two pairs of the neighboring wings can be the same while the third pair is spaced at a different distance. In some embodiments, in lieu or in addition to changing the distance between the wings 34 to vary the size of the gaps 44, widths (distance between the elongated tube 32 and vacuum lumen 40) of the wings can vary so provide gaps 44 of different sizes. By provided wings 34 having different widths, the position of the laser head will be shifted relative to the center of the vacuum lumen. Accordingly, in some embodiments, at least two different sized gaps 44 can be provided.

Figure 6:
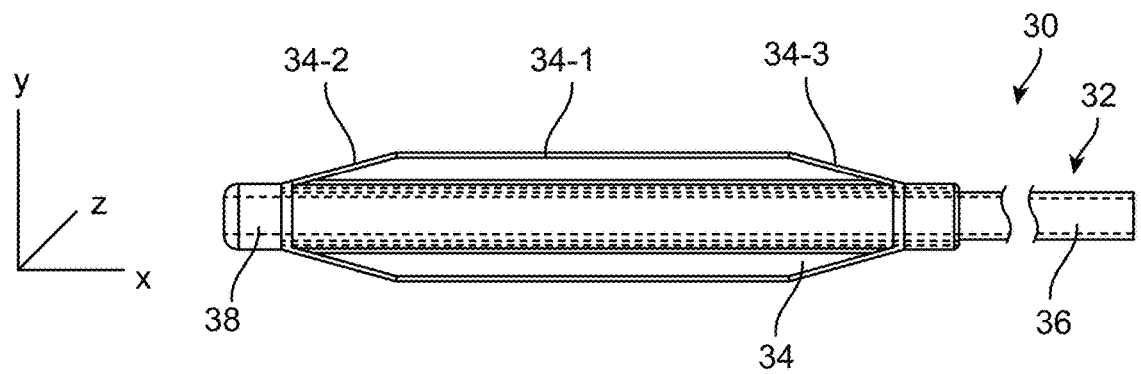
FIG. 6 is a schematic view of a distal section of an embodiment of the guide.
Figure 7A:
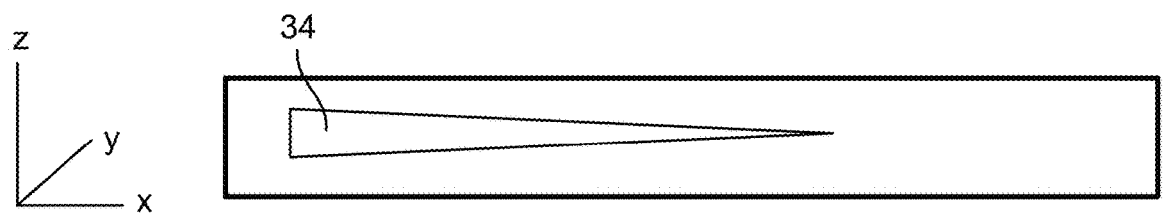
FIGS. 7A and 7B are top plan views illustrating various embodiments of wings or extensions for the guide.
Figure 7B:

FIG. 6 is an embodiment of the wing 34 design. The wing 34 includes a middle section 34-1 extending into a distal 34-2 and proximal 34-3 segments. The length (in the x-direction, i.e., along the longitudinal axis) of the middle section 34-1 is greater than the length of the distal 34-2 and proximal 34-3 segments. The middle section 34-1 can have a constant width (in the y-direction, i.e., along the radial axis). The middle section 34-1 can have a rectangular shape, which allows it to have sufficient surface contact with an inner side of the vacuum lumen to create stability and prevent any unintended shifting of the guide's 30 distal end, where the wings 34 are located. The distal 34-2 and proximal 34-3 segments of the wing 34 slope or taper from the middle section 34-1 to the elongated tube 32. The thickness (in the z-direction) of the wing 34 can be the same along its entire span. In an alternative embodiment, the thickness (in the z-direction) of the wing 34 can vary so that the wing 34 is tapered along the x- or longitudinal direction. For example, as best illustrated in FIG. 7A, the wing 34 can have its thickest dimension at its leading, distal end and its thinnest dimension in its proximal end. In one embodiment, the sidewalls of the wing 34 can converge at an angle, as is shown in FIG. 7A, to provide the wing 34 with a shape of an isosceles triangle when viewed from the top. In accordance with another embodiment, as illustrated in FIG. 7B, the longitudinal axis of the wing 34 is not aligned with the longitudinal x-axis of the guide 30. The longitudinal axis of the wing 34 is rotated with respect to the x-axis of the guide 30. In accordance with another embodiment, not illustrated, the wings 34 can have a radius of curvature long the longitudinal direction. The wings 34 can be positioned symmetrically around the elongated body 32, or alternatively, the wings 34 are positioned asymmetrically around the elongated body 32.

Figure 8:
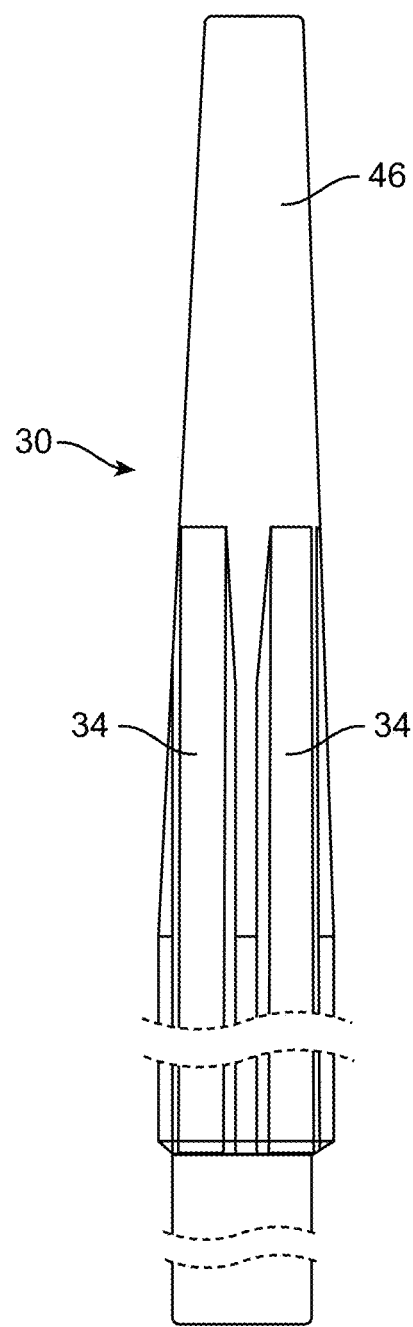
FIG. 8 is a partial side plan view of an embodiment of the guide.

FIG. 8 illustrates another embodiment of the guide 30. The guide 30 includes a distal end section 46 that is configured to extend out of the vacuum lumen when the guide 30 is placed in position. The distal end section 46 can be a soft tip, for example. The wings 34 are positioned proximal to the distal end section 46, but are intended to reside at the distal end segment of the vacuum tube.

Figure 9A:
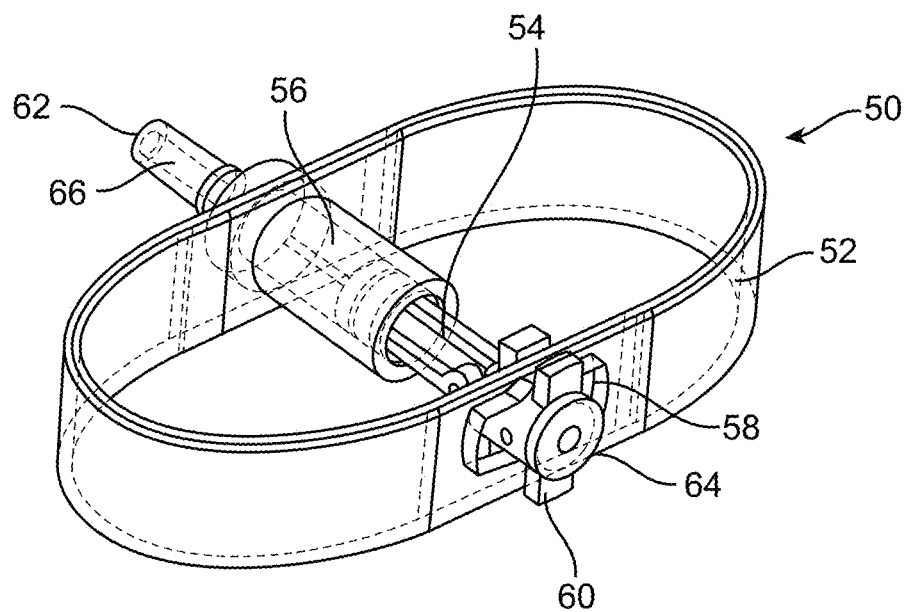
FIG. 9A is a perspective view of an embodiment of an actuator to actuate the guide.
Figure 9B:
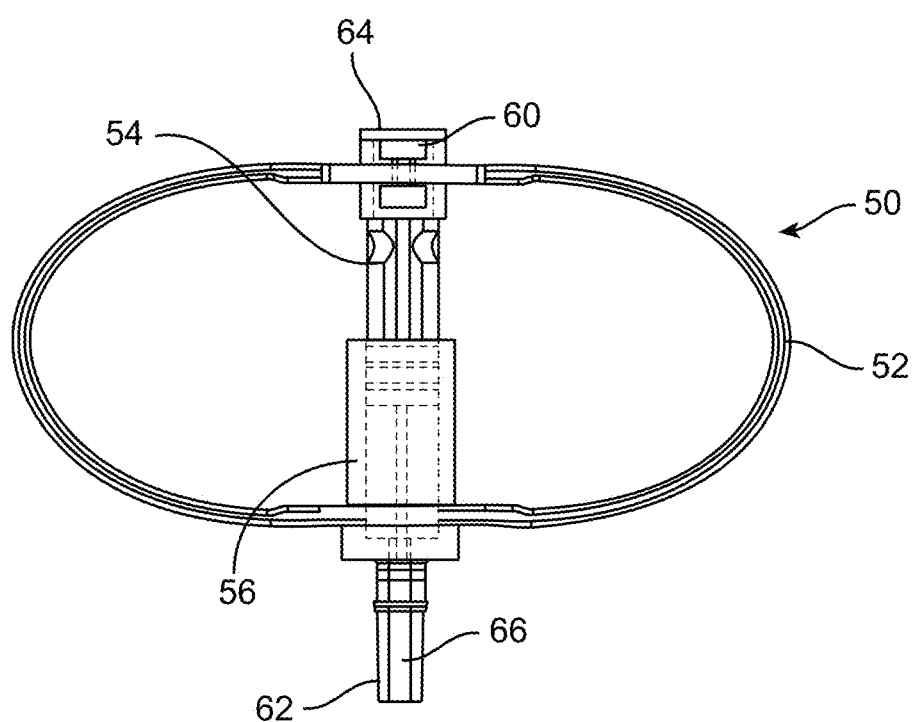
FIG. 9B is a top plan view of an embodiment of the actuator.

The guide 30 fixedly supports the head of the laser fiber at the distal tip of a vacuum lumen while allowing the vacuum lumen to aspirate stones, debris, and fluids during the laser procedure and concomitantly with the fragmentation of kidney stones. However, the presence of the guide 30 reduces the inner working diameter of the vacuum lumen. Thus, the guide 30 increases the chance of larger sized stones gathered and/or becoming lodged at the entry point of the vacuum lumen, as well as in the gaps 44 or between the wings 34. Such clogging can reduce evacuation efficiency and require manual debris clearance or increasing internal pressures. Accordingly, a device can be used to cause back-and-forth movement, vibration, or oscillation of the guide 30 to clear or extricate lodged or clogged stones. Minor back-and-forth movement of the guide 30 can be effective at dislodging debris and clearing the vacuum lumen. In accordance with one embodiment, as illustrated in FIGS. 9A and 9B, an actuator 50 is provided that can be permanently attached to or removable coupled with the guide 30. The actuator 50 can include a biasing band 52. The biasing band 52 is a self-resetting body, such that the inward compression (i.e., squeezing) and release of the band 52 can cause the back-and-forth movement of the guide 30 and the wings 34 within the vacuum lumen. A shaft 54 has one end penetrating through a hole 58 of the band 52. The shaft 54 can be fixedly secured to the band 52 by two pairs of opposing tabs 60 extending from the shaft 54. A cylindrical housing 56 receives an opposing end of the shaft 54. The shaft 54 can move telescopically, back-and-worth, within the cylindrical housing 56 when the band 52 is compressed and released. The cylindrical housing 56 is coupled to the opposing side of the band 52 to which the shaft 54 is coupled. The shaft 54 can include a shaft head 64 that can be permanently attached to a proximal tail of the guide 30, or alternatively, the shaft head 64 can be configured to be able to be removably coupled to the proximal tail of the guide 30. For example, the shaft head 64 and the proximal tail of the guide 30 can have female/male coupling members. A tubular member 62 can extend from the proximal end of the cylindrical housing 56. The member 62 can be configured to connect to and disconnect from a handle (e.g., handle 12) of a catheter. An access channel 66 can extend from the member 62, the cylinder housing 56, and the shaft 54 and communicate with the lumen 36 of the guide 30. The laser fiber can be inserted into the inlet opening of the access channel 66, fed through the actuator 50, and inserted into the lumen 36 of the guide 30. The laser fiber can be pushed through the lumen 36 of the guide 30 until the laser's head reaches the distal tip of the vacuum lumen, where wings 34 of the guide 30 prevent any unintended movement of the laser's head.

Figure 10:
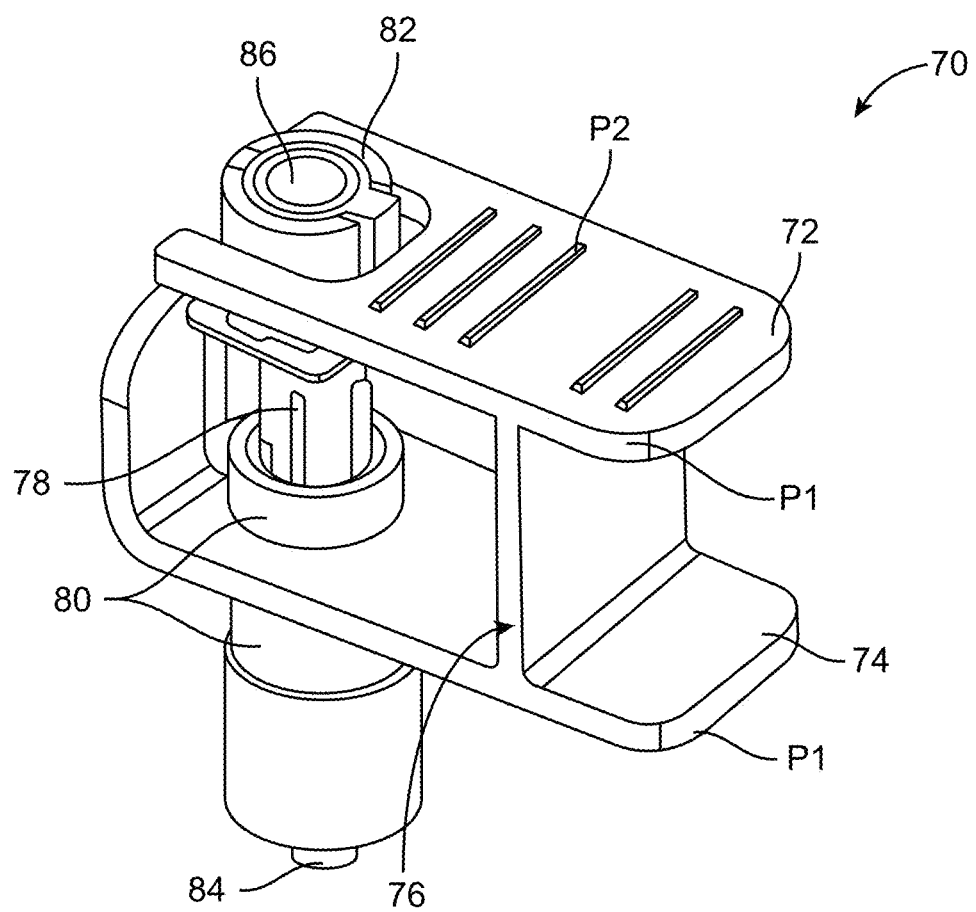
FIG. 10 is a perspective view of an embodiment of the actuator.

FIG. 10 illustrates another embodiment of an actuator 70. The actuator 70 can be permanently attached to or removably coupled with the guide 30. The actuator 70 can include a first (or as oriented in the figure, an upper or distal) lever 72 coupled to a second (or lower or proximal) lever 74 via a fulcrum bar 76. The actuator 70 is self-resetting, such that the inward compression (i.e., squeezing) and release of levers 72 and/or 74 can cause the back- and forth movement of the guide 30 and the wings 34 within the vacuum lumen. A shaft 78 is coupled to the upper lever 72 and extends out of an opening of the upper lever 72. A cylindrical housing 80 receives an opposing end of the shaft 78. The shaft 78 can move telescopically, back-and-forth, within the cylindrical housing 80 when levers 72 and/or 74 are compressed and released. The cylindrical housing 80 is coupled to the lower lever 74. The shaft 78 includes a shaft head 82 that can be permanently attached to a proximal tail of the guide 30, or alternatively, the shaft head 82 can be configured to be able to be removably coupled to the proximal tail of the guide 30. For example, the shaft head 82 and the proximal tail of the guide 30 can have female/male coupling members. A tubular member 84 can extend from the proximal end of the cylindrical housing 80. The tubular member 84 can be configured to connect to and disconnect from a handle (e.g., handle 12 described above) of a catheter. A channel 86 is accessible from the member 84, and can extend from the member 84, the cylindrical housing 80, and the shaft 78, and communicate with the lumen 36 of the guide 30. The laser fiber can be inserted into the inlet opening of the access channel 86, fed through the actuator 70, and inserted into the lumen 36 of the guide 30. The laser fiber can be pushed through the lumen 36 of the guide 30 until the laser's head reaches the distal tip of the vacuum lumen or nozzle tip, where the wings 34 of the guide 30 prevent any unintended movement of the laser fiber's head. In operation, if the actuator 70 is squeezed inward at position P1 (e.g., the upper lever 72 and lower lever 74 are pinched towards each other), the shaft 78 actuates outwards (upwards in the illustration) and away from the lower lever 74). Here, the upper lever 72 and/or lower lever 74 pivot about the fulcrum arm 76 to create a wider gap between the levers 72/74 at the shaft end of the actuator 70 and a smaller gap between the levers 72/74 at the end labeled position P1. If the actuator 70 is squeezed inward at position P2, (e.g., the upper lever 72 and lower lever 74 are pinched towards each other or the upper lever 72 is pushed downwards towards the lower lever 74), the shaft 78 actuates inwards (downwards in the illustration) and towards the lower lever 74). Here, the upper lever 72 and/or lower lever 74 pivot about the fulcrum arm 76 to create a smaller gap between the levers 72/74 at the shaft end of the actuator 70 and a wider gap between the levers 72/74 at the end labeled position P1. Thus, the movement of the shaft head 82 can be either away from or towards the lower lever 74 based on the force that is applied either at P1 or P2.

FIG. 11A illustrates a front-end view of another embodiment of a guide 100. The guide 100 includes an elongated tube 100 that is sized to accommodate a laser fiber 42. The guide 100 may optionally have features extending from the outer surface of the elongated tube 110 to contact the inner surface of a vacuum tube (not pictured). FIG. 11B and FIG. 11C each illustrate a partial side plan view of different embodiments of a guide 100. In FIG. 11B, the guide 100 includes an elongated tube 110 and a distal portion have a curved section 120. In FIG. 11C, the guide 100 includes an elongated tube 110 and a distal portion have a first curved section 120 and a second curved section 130. In each of these embodiments, the curved sections 120, 130 function to bias the guide 100 and constitute one or more pre-formed bends or curves in in distal region of the guide 100. These curved sections 120, 130 bias the distal region of the guide 100 against an inner surface of the vacuum tube (or other lumen of the device if an irrigation lumen or working lumen is used for the insertion path of the guide 100). The guide 100 is preferable formed using materials, combinations of materials, assemblies, or sub-assemblies that have comparatively high torsional rigidity and thereby provide comparatively high torque transmission from a proximal portion of the guide 100 to the distal portion of the guide 100. This high torque transmission allows a user to rotate the guide 100 relatively easily to further position the guide (and the laser fiber 42 when the lase fiber is present). In this manner, the guide 100 can assist in targeting the laser fiber 42 with a vacuum lumen or other lumen.

In some embodiments, the guide 100 can come in a kit that includes a loading element that straightens the curved sections 120, 130 to facilitate insertion of the laser fiber 42. After insertion of the laser fiber 42, the loading element is removed and the guide 100 assumes its pre-formed/biased shape with the laser fiber 42 inside the guide 100.

Figure 12:
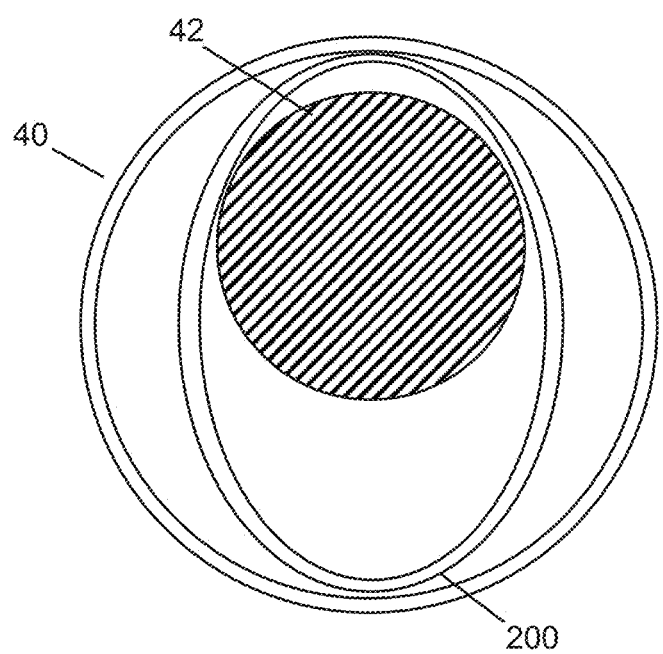
FIG. 12 is a front-end view of an embodiment of a guide positioned inside a vacuum tube.

FIG. 12 is a front-end view of an embodiment of a guide 200 positioned inside a vacuum tube 40. In this embodiment, the guide 200 includes an elongated tube in which at least the distal portion of the elongated tube has a cross-section (i.e., cross-sectional perimeter) that is not symmetric about its center (longitudinal) axis. In the embodiment illustrated in FIG. 12, the cross-section has an elliptical or oval shape. The asymmetric cross-section of the guide 200 biases the rotational movement of the guide 200. Thus, other asymmetric cross-sections that similarly bias the rotational movement of the guide 200 are also contemplated. And such asymmetric cross-sections can be used in conjunction with the curved sections disclosed herein to provide multiple methods for biasing the guide 200 against the inner surface of the vacuum lumen or other lumen to provide a stable orienting method for positioning the laser fiber 42. Further, the asymmetric cross-section allows for gaps between the inner surface of the vacuum tube 40 and the outer surface of the guide 200 to provide flow through the vacuum tube 40 to enable removal of stone fragments, fluid, and other debris.

Figure 13:
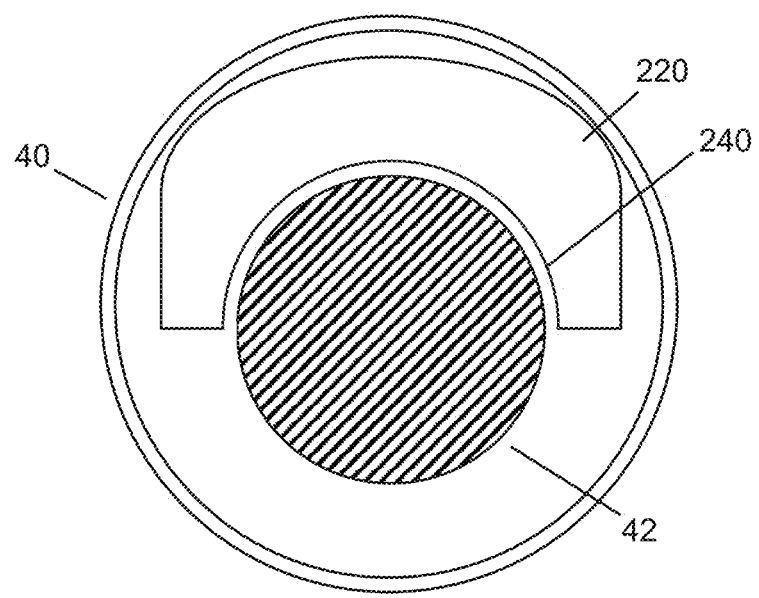
FIG. 13 is a front-end view of another embodiment of a guide positioned inside a vacuum tube.

FIG. 13 is a front-end view of another embodiment of a guide 220 positioned inside a vacuum tube 40. In this embodiment, the guide 220 includes an elongated tube in which at least a distal portion of the elongated tube has a cross-section that is not symmetric about its center axis. In the embodiment illustrated in FIG. 13, the cross-section has a D-shape that includes a groove or channel 240 for accommodating the laser fiber 42. The distal cross section can also be considered as being C-shaped or inverted U-shaped. The distal shape (e.g., D shaped, C-shaped, or inverted U-shaped) of the guide 220 provides both a shape complementary to the curved inner surface of the vacuum tube 40, enabling stable contact to facilitate positioning the laser fiber 42, and a shape that allows for a sizable gap between the inner surface of the vacuum tube 40 and the outer surface of the guide 220 to provide flow through the vacuum tube 40 to enable removal of stone fragments, fluid, and other debris. The curved side of the D-shape (or C- or U-shape), opposing the groove 240, can have a radius of curvature different from the radius of the curvature of the inner wall of the vacuum tube 40. Accordingly, a smaller gap can be present between the curved side and the inner wall of the vacuum tube 40. The groove 240 can be formed to substantially match the radius of curvature of the laser fiber 42 and can have the radial arc of a semi-circle, more than a semi-circle, or less than a semi-circle.

Figure 14:
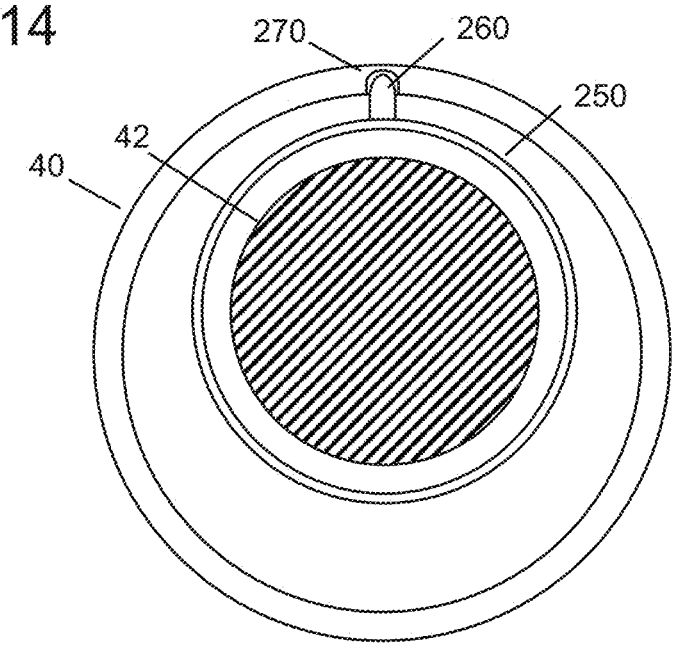
FIG. 14 is a front-end view of another embodiment of a guide positioned inside a vacuum tube.

FIG. 14 is a front-end view of another embodiment of a guide 250 positioned inside a vacuum tube 40. In this embodiment, the guide 250 includes a first mechanical feature that is configured to mechanically or physically engage with a second mechanical feature of the vacuum tube 40. In one embodiment, the guide includes a projecting feature 260 that engages with a receiving feature 270 in the wall of the vacuum tube 40. The projecting feature 260 and receiving feature 270 interact mechanically to provide repeatable positioning of the guide 250 and laser fiber 42 when they are advanced to the distal potion of the vacuum tube 40. The projecting feature 260 and receiving feature 270 interact to prevent unwanted rotational or other movement of the guide 250 with respect to the vacuum tube 40. The projecting feature 260 and receiving feature 270 can each independently extend along some or all of the distal portion of the guide 250 and the vacuum tube 40, respectively. In some embodiments, the receiving feature 270 extends along substantially all of the inner surface of the vacuum tube 40 and functions as a guiding track to engage with the projecting feature 260 of the guide 250 and facilitate advancement of the guide 250 from a proximal end of the vacuum tube 40 to the distal portion of the vacuum tube 40. In this embodiment, the guide 250 can be sized to allow for a substantial gap between the inner surface of the vacuum tube 40 and the outer surface of the guide 250 to provide flow through the vacuum tube 40 to enable removal of stone fragments, fluid, and other debris.

Figure 15:
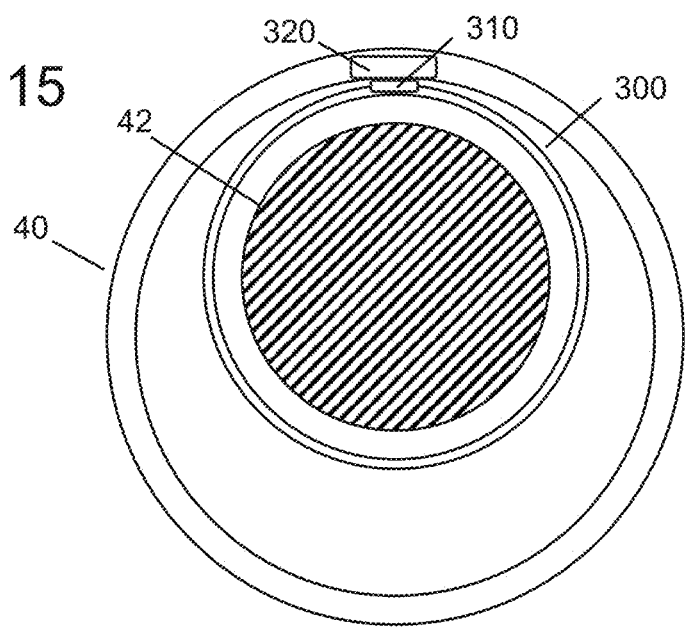
FIG. 15 is a front-end view of another embodiment of a guide positioned inside a vacuum tube.

FIG. 15 is a front-end view of another embodiment of a guide 300 positioned inside a vacuum tube 40. In this embodiment, the guide 300 includes one part of a pair magnetic features where a pair of magnetic feature means: a magnetized material and a magnetically attractable material or two magnetized materials oriented to attract each other. FIG. 15 illustrates that the guide 300 includes a magnetic feature 310 and the vacuum tube 40 includes the magnetic feature 320. Each of the magnetic features 310, 320 can be included on the surface or within the tube wall of guide 300 and vacuum tube 40, respectively. Each of the guide 300 and the vacuum tube 40 can include one or more of the magnetic features 310, 320. A pair of magnetic features 310, 320 interact to bias the guide 300 towards the inner surface of the vacuum tube 40 and/or to pull the guide 300 towards the distal end of the vacuum tube 40. In some embodiments, the guide 300 is a simple ring placed around the distal position of the laser fiber 42 and the included magnetic feature 310 interacts with the magnetic feature 320 of the vacuum tube 40 when the laser fiber 42 is advanced towards the distal end of the vacuum tube 40. In other embodiments, the entire guide 300 is a simple ring placed around the distal position of the laser fiber 42 and the ring itself is a magnetic feature capable of being attracted to magnetic feature 320 of the vacuum tube 40. In this embodiment, the guide 300 can be sized to allow for a substantial gap between the inner surface of the vacuum tube 40 and the outer surface of the guide 300 to provide flow through the vacuum tube 40 to enable removal of stone fragments, fluid, and other debris.

Figure 16A:
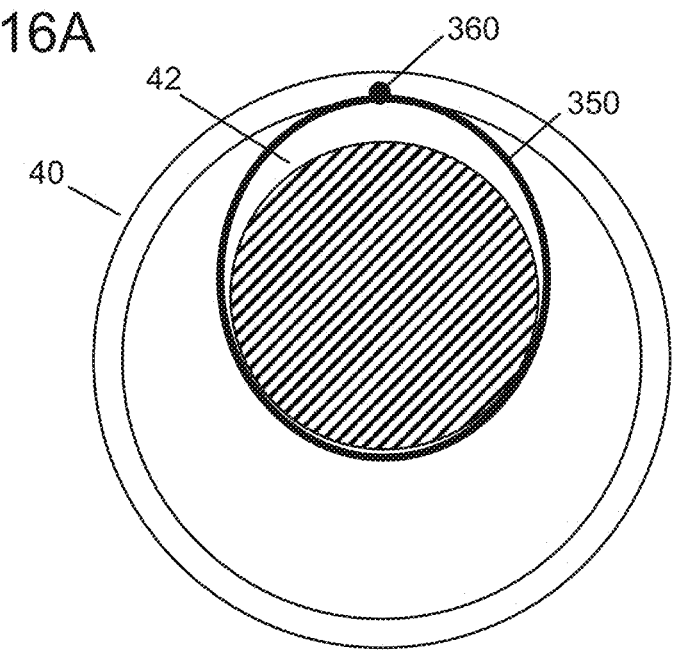
FIG. 16A is a front-end view of an embodiment of a vacuum tube including a guide feature.
Figure 16B:
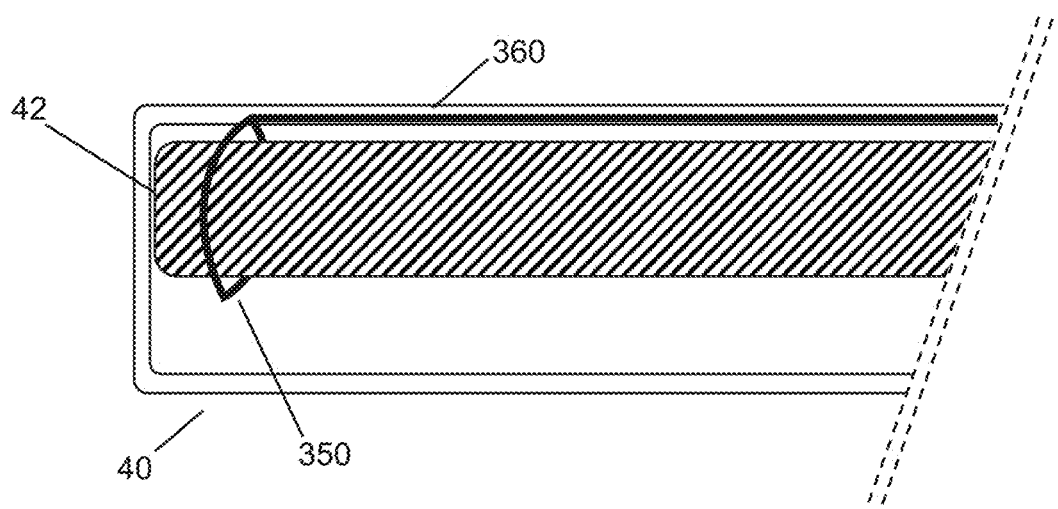
FIG. 16B is a schematic partial side view of an embodiment of a vacuum tube including a guide feature.

FIG. 16A is a front-end view of an embodiment of a vacuum tube including a guide feature and FIG. 16B is a schematic partial side view of the embodiment. This embodiment includes a capturing feature integral with the vacuum tube 40 in the form of a snare 350 coupled with an activation feature 360. A laser fiber 42 is advanced to the distal portion of the vacuum tube 40 and through the loop formed by the snare 350. The activation feature 360 is then engaged to capture the laser fiber 42 more fully within the snare 350 by, for example, reducing the size of the loop in the snare 350 such that it secures the laser fiber 42 and prevents it from moving more than is desired during operation of the laser. In other embodiments, the snare 350 can be formed from a temperature sensitive material such as nitinol activated by changes in local temperature at the distal portion of the vacuum tube 40. The local changes in temperature can be accomplished by applying heated or cooled fluid to the distal portion of the vacuum tube 40, by temperature conduction along the vacuum tube 40, by temperature conduction along the activation feature 360, or by combinations thereof. Notably, the snare 350 or other equivalent capturing feature integral with the vacuum tube is retractable such that it has a substantially reduced profile when not engaging the laser fiber 42 and thereby help maximize the cross-section of the vacuum tube 40 when in such a reduced profile.

Figure 17A:
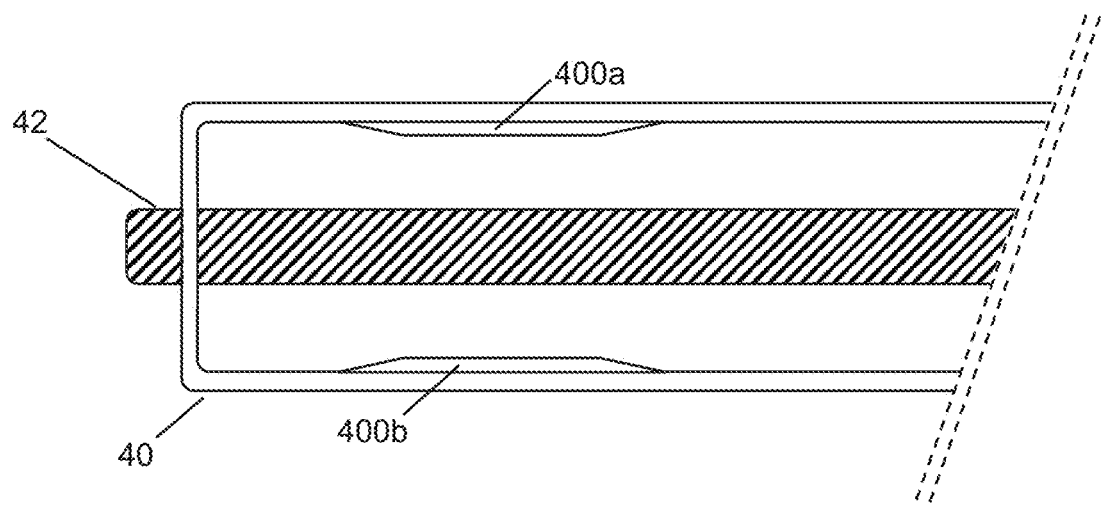
FIG. 17A is a schematic partial side view of an embodiment of a vacuum tube including a guide feature.
Figure 17B:
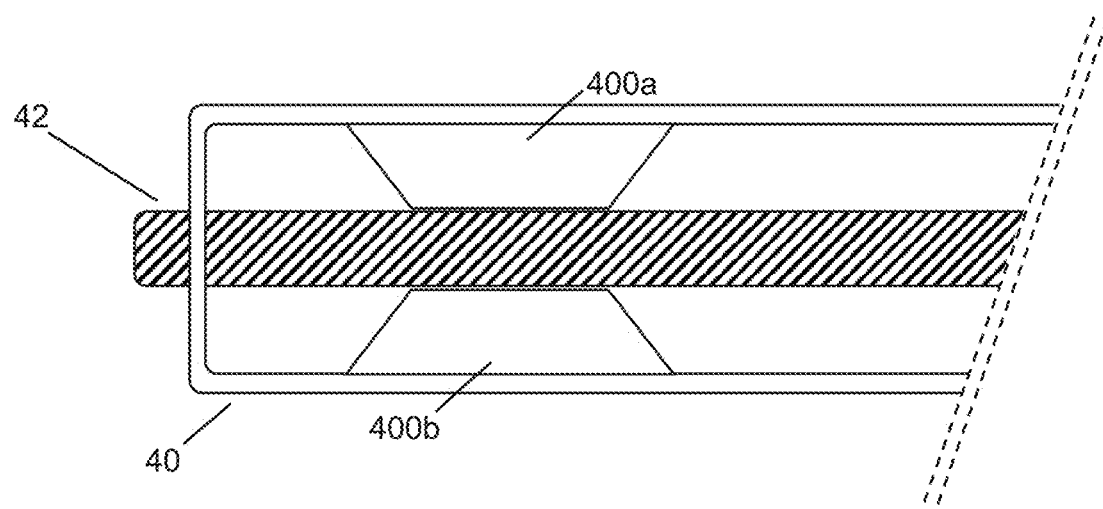
FIG. 17B is a schematic partial side view of an embodiment of a vacuum tube including a guide feature.

FIG. 17A is a schematic partial side view of an embodiment of a vacuum tube including a guide feature and FIG. 17B is a schematic partial side view of the embodiment. FIG. 17A and FIG. 17B illustrate another embodiment of a capturing feature integral with the vacuum tube 40, and in this embodiment the capturing feature includes selectively expandable sections 400a, 400b. In some embodiment, the selectively expandable sections 400a, 400b are formed from an inner liner in the wall of the vacuum tube 40 such that the selectively expandable sections 400a, 400b can be inflated or expanded (for example, like a balloon with application of a fluid such as saline) in an equivalent manner to capture the laser fiber 42 when it is at the distal portion of the vacuum tube 40. There may be a single selectively expandable section, multiple selectively expandable sections, paired selectively expandable sections, expandable sections of different sizes, or combinations thereof. In an embodiment, the expandable sections are sized and/or positioned to allow for substantial gap(s) between the expandable sections to provide flow through the vacuum tube 40 and passed the expandable sections to enable removal of stone fragments, fluid, and other debris. The selectively expandable sections 400*a*, 400*b* or other equivalent capturing feature(s) integral with the vacuum tube 40 are retractable such that the features have a substantially reduced profile when not engaging the laser fiber 42 and thereby help maximize the cross-section of the vacuum tube 40 when in such a reduced profile.

Figure 18:
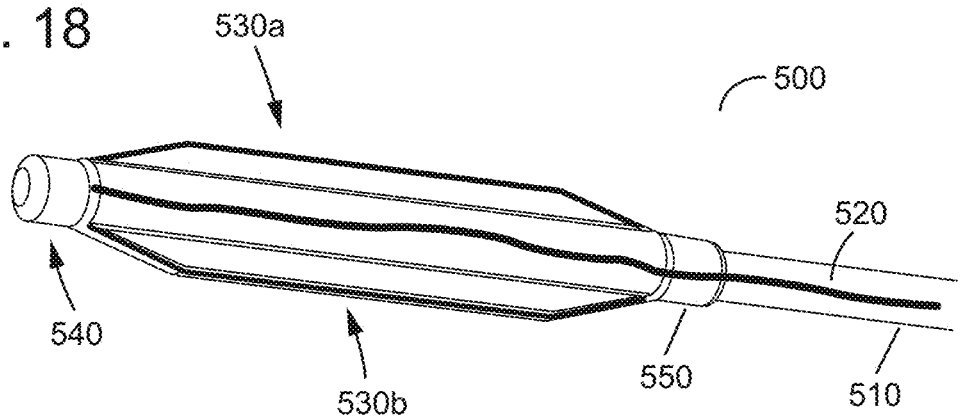
FIG. 18 is a perspective view of an embodiment of a guide.

FIG. 18 is a perspective view of an embodiment of a guide 500. An elongated tube 510 includes an activation wire 520 coupled to a sliding end cap 540 that can slide in a proximal direction towards a fixed proximal cap 550 when activated by the activation wire 520. The sliding motion of the end cap 540 deploys one or more wings or extensions 530*a*, 530*b* that are configured to engage against the inner wall or surface of a vacuum tube (not pictured). The extensions or wings 560 can project out radially to secure the guide 500 to the vacuum tube. There may be a single wing or multiple wings 530. The wings 530 can be of suitable size, shape, and/or number to allow for substantial gap(s) between and/or around the wings 530 to provide flow past the wings 530 and through the vacuum tube to enable removal of stone fragments, fluid, and other debris. The wings 530, when not in a deployed or radially expanded position, should provide a substantially reduced profile and thereby help maximize the cross-section of the vacuum tube when in such a reduced profile.

In certain embodiments disclosed herein, it can be advantageous to use a loading mechanism for the laser fiber to assist with placing the laser fiber within a guiding feature in a vacuum tube. One example of a loading mechanism is a cap to be temporarily placed over the tip of the laser fiber, where the tip acts as a feature like a hole, a loop, or a projection that helps orient the laser fiber to the guiding feature in the vacuum tube.

Figure 19A:
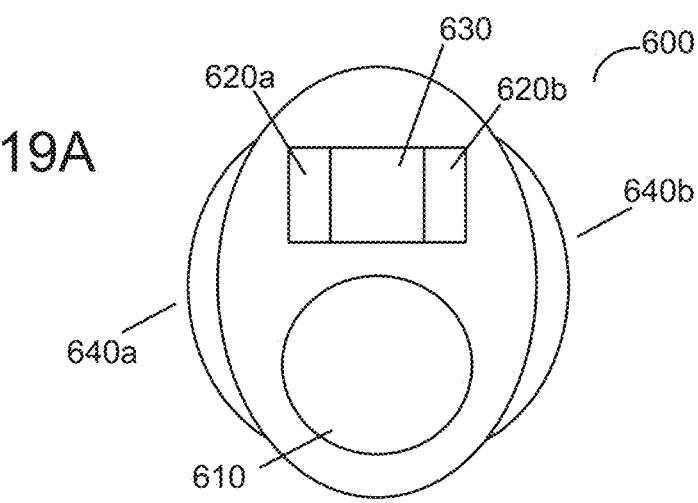
FIG. 19A is a front-end view of an embodiment of a ureteroscope including a guide feature.
Figure 19B:
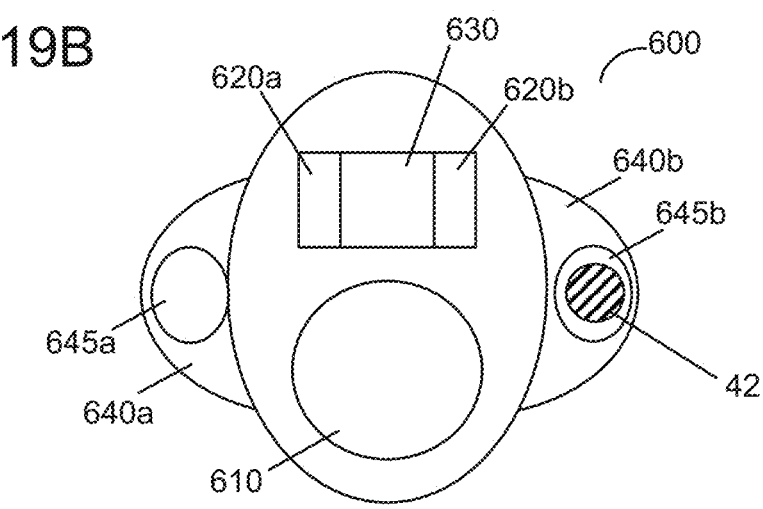
FIG. 19B is a front-end view of an embodiment of a ureteroscope including a guide feature.

FIG. 19A and FIG. 19B are each a front-end view of an embodiment of a ureteroscope 600 including a guide feature. The ureteroscope 600 includes a vacuum lumen 610, lighting features 620*a*, 620*b* (for example, LEDs or the equivalent), and vision feature 630 (for example, a CCD camera). The ureteroscope 600 also includes expandable features 640*a*, 640*b* that may be actively expandable (such as by inflation) to yield channels 645*a*, 645*b* or may be passively expandable by inserting a laser fiber 42 through a channel 645*a* or 645*b*. In some embodiments, the channels 645*a*, 645*b* are used for irrigation by sending irrigation fluid through the channels 645*a*, 645*b* prior to or after expansion of the expandable features 640*a*, 640*b*. In some embodiments, sending fluid through the channel 645*a*, 645*b* acts to expand the expandable features 640*a*, 640*b*. FIG. 19B illustrates an embodiment in which channel 645*b* is being used as a working channel for the laser fiber 42 and thereby channel 645*b* is functioning as a guide for the laser fiber 42. One notable benefit of these embodiments is that the ureteroscope has a smaller overall cross-section when the expandable features 640*a*, 640*b* are unexpanded, which can allow the ureteroscope to access more easily certain anatomy prior to the laser fiber 42 being inserted into channel 645*a* or 645*b*.

Figure 20A:
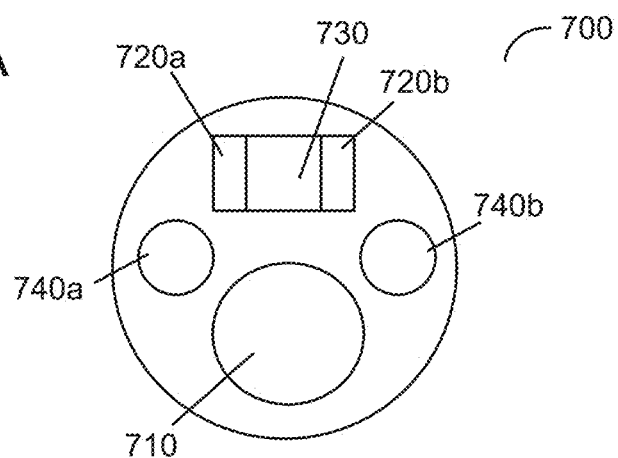
FIG. 20A is a front-end view of an embodiment of a ureteroscope including a guide feature.
Figure 20B:
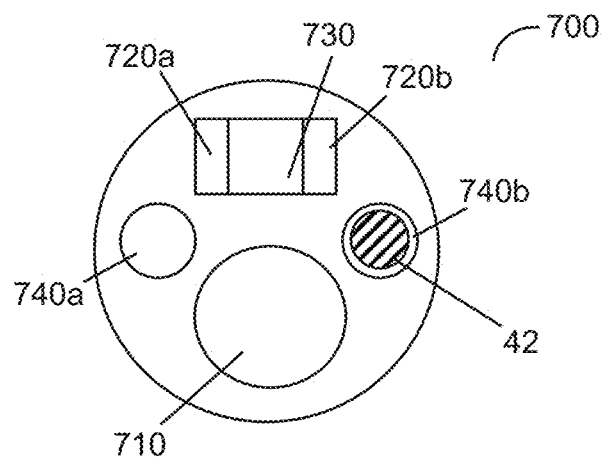
FIG. 20B is a front-end view of an embodiment of a ureteroscope including a guide feature.

FIG. 20A and FIG. 20B are each a front-end view of an embodiment of a ureteroscope 700 including a guide feature. The ureteroscope 700 includes a vacuum lumen 710, lighting features 720*a*, 720*b* (for example, LEDs or the equivalent), and vision feature 730 (for example, a CCD camera). The ureteroscope 700 further includes channels 740*a*, 740*b* that can be used independently for irrigation or for guiding a laser fiber 42.

Figure 21:
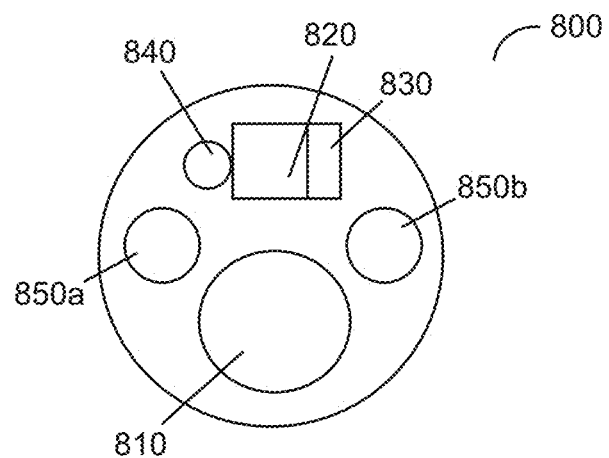
FIG. 21 is a front-end view of an embodiment of a ureteroscope.

FIG. 21 is a front-end view of an embodiment of a ureteroscope 800. The ureteroscope 800 includes a vacuum lumen 810, vision feature 820 (for example, a CCD camera) and dedicated lighting feature 830 (for example, LEDs or the equivalent). The ureteroscope includes a configurable lighting feature 840 that can function as lighting is some circumstances and can provide laser energy in other circumstances. The ureteroscope 800 further includes channels 850*a*, 850*b* that can be used independently for irrigation, and other configurations of irrigations channels are contemplated for use with this embodiment.

Referring still to FIG. 21, in some embodiments the configurable lighting feature 840 is a light fiber lumen that can accommodate a visible light fiber or a laser fiber. During non-laser operation, a visible light fiber is in place in the lumen to provide additional illumination. During lasering, that fiber is replaced (or only swapped on the back end) to a laser fiber. In some embodiments, the configurable lighting feature 840 is a light pipe or light fiber than can alternately transmit visible light or laser light. The light pipe or light fiber can provide diffuse optical light, focused optical light, or laser light depending on the desired operation by the user.

Other embodiments of a laser guide include a laser guide formed from multiple optical fibers surrounding a central lumen through which as laser fiber can be introduced. In this embodiment, a working channel is used for both lighting and the laser and this frees some of the cross-section of the device to be used for irrigation lumen(s) and/or vacuum lumen(s).

Other embodiments of a laser guide include using water jets or vacuum flow to maintain the laser fiber position within the vacuum lumen. The water jets can engage the laser fiber at a position beyond the end of the vacuum lumen to maintain the position of the laser fiber with respect to the vacuum lumen. The water jets are generated by ports on the guide or on the device in which the guide is inserted. Alternatively or in combination, the vacuum lumen can be configured to produce fluid flow through the vacuum lumen that engages the laser fiber within the vacuum lumen to maintain the position of the laser fiber with respect to the vacuum lumen.

Other embodiments of a laser guide include a steerable guide with at least one steering wire that can be steered separately and in conjunction with the steering of the main catheter. The steering of the guide can be locked into place or locked into steered configuration (i.e., a curved shape).

While the following embodiment of method of use is described with reference to FIG. 3, this use embodiment is applicable to all embodiments, devices, and aspects described above. For the treatment of kidney stones, the catheter can be directed into the kidney with a use of guidewire. The guide 30 can be inserted into the vacuum lumen before the insertion of the catheter into the patient. The lumen 36 of the guide can be used to receive the guidewire for navigating the catheter over the guidewire. Alternatively, the guide 30 can be inserted into the catheter at any time during the procedure, including when the catheter has reached its intended position. If a guidewire is with the lumen 36, the guidewire is removed followed by insertion of the laser fiber. The laser fiber is directed through the lumen 36 of the guide 30 until the laser's head reaches the end of the knob 38. A physician can apply laser pulses to kidney stones concomitantly with aspirating debris, stones, and fluids through the catheter's vacuum lumen. Should any stones become lodged at the opening of the guide 30, the actuator 50 can be used to move the guide 30 within the vacuum lumen to dislodge the stones. After the laser procedure, the guide 30 can be removed and the vacuum lumen can be used for the extraction of the remaining un-fragmented or fragmented stones.

The various examples, aspects, and embodiments of the kidney stone removal systems disclosed herein provide various advantages when used to treat kidney stones. These advantages are being provided by way of illustration and are not intended to limit the scope of the claims. One advantage is the ability to prevent or to mitigate the possibility of overpressurizing the kidney during kidney stone treatment. In conventional laser lithotripsy of kidney stones, irrigation fluid can be introduced during ureteroscopy and/or during laser lithotripsy. In most cases, the irrigation fluid can drain out of the kidney only via the narrow space between the ureteroscope and the access sheath. This narrow space can become narrowed further by debris such as kidney stone fragments, clots, or other substances. When the egress of fluid from the kidney is limited by such a narrow space, continued infusion of irrigation fluid creates the risk of high pressures in the kidney, which can cause sepsis and/or other complications. The kidney stone removal system disclosed herein provides a much larger egress channel via the large diameter vacuum lumen. Further, it is possible to apply vacuum through the large diameter vacuum lumen while introducing irrigation fluid. The large diameter of the vacuum lumen in combination with the ability to apply vacuum while delivering irrigation fluid significantly reduces the likelihood of overpressurizing the kidney, resulting in safer kidney stone removal procedures.

Another advantage of the kidney stone removal systems disclosed herein is the ability to prevent or mitigate thermal damage to the kidney during laser lithotripsy. Heat is generated within the kidney during laser lithotripsy of kidney stone, in particular with higher power lasers. This heat can be damaging to the kidney and is a concern for physicians when performing laser lithotripsy. Irrigation fluid can help dissipate the heat via conductive heat transfer, but as described herein irrigation fluid can also build up within the kidney if the pathway for draining is relatively narrow. The kidney stone removal system disclosed herein provides a much larger egress channel via the large diameter vacuum lumen in combination with the ability to apply vacuum while delivering irrigation fluid. The kidney stone removal system disclosed herein can maintain a safe temperature within the kidney by rapidly removing heated irrigation fluid from the kidney and introducing relatively cooler irrigation fluid in a continuous manner during laser lithotripsy. In the examples, aspects, and embodiments of the kidney stone removal system that include a laser guide, heated irrigation fluid can easily and rapidly flow through the vacuum lumen even while the laser fiber is being used to fragment kidney stones and comparatively cooler irrigation fluid can easily and rapidly enter the kidney via the irrigation ports on the nozzle. This rapid heat transfer via irrigation fluid rapidly introduced and removed from the kidney significantly reduces the likelihood of thermal damage to the kidney, resulting in safer kidney stone removal procedures.

Another advantage of the kidney stone removal systems disclosed herein is the ability to improve visibility in the kidney during laser lithotripsy. In conventional laser lithotripsy, debris from fragmenting kidney stones frequently obscures the view from the imaging portion of a ureteroscope and makes it difficult for a physician to see areas of interest within the kidney and/or the kidney stones being fragmented. Physicians often describe a "snow globe" effect during laser lithotripsy in which debris is ejected from the kidney stone in a random and chaotic manner that quickly fills their field of view. The kidney stone removal system disclosed herein can improve visibility by rapidly removing debris fluidized in the irrigation fluid from the kidney through the large diameter vacuum lumen and introducing clear irrigation fluid in a continuous manner during laser lithotripsy. In the examples, aspects, and embodiments of the kidney stone removal system that include a laser guide, debris suspended or fluidized in irrigation fluid can easily and rapidly flow through the vacuum lumen even while the laser fiber is being used to fragment kidney stones. Further, rather than a random and chaotic field of view, the kidney stone removal system disclosed herein provides a predictable pattern as debris moves in a regular motion across the field of view to the vacuum lumen. Such a regular pattern makes it easier for a physician to stay oriented with anatomical landmarks in the field of view. Still further, because of the comparatively large egress channel (as compared to the narrow channel between the ureteroscope and access sheath) more debris is removed and removed faster using the kidney stone removal system disclosed herein. In some cases, even with little or no applied vacuum the large diameter of the vacuum lumen creates sufficient passive outflow to substantially improve visibility. The large diameter of the vacuum lumen in combination with the ability to apply vacuum while delivering irrigation fluid and in combination with the regular debris flow pattern significantly improves visibility during laser lithotripsy, resulting in safer, more efficient, and more effective kidney stone removal procedures.

Another advantage of the kidney stone removal systems disclosed herein is the ability to rapidly apply and remove therapeutic or diagnostic agents in the kidney during laser lithotripsy. The irrigation fluid can have chemical or biological agents applied to it from the source bag or using a port adjacent to the system handle. These agents can be therapeutic, such as, but not limited to, hemostatic, antibiotic, and/or lytic agents. And these agents can be diagnostic, such as, but not limited to, contrast agents.

Another advantage of the kidney stone removal systems disclosed herein is that the irrigation ports can provide a flow rate independent of the tool being used within the vacuum lumen. Conventional ureteroscopes typically provide irrigation through the working channel and this same working channel is used to provide access for laser fibers or baskets. The presence of a tool within the working channel alters the fluid dynamics and changes the flow rate and other flow characteristics. In contrast, the kidney stone removal systems disclosed herein delivers irrigation fluid via dedicated irrigation ports such that the flow characteristics are independent of the tool being used, if any, in the vacuum lumen.

It is understood that this disclosure, in many respects, is only illustrative of the numerous alternative device embodiments of the present inventions. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the inventions are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A kidney stone removal system, comprising:
   (a) a kidney stone removal catheter configured for insertion into a kidney for treatment of kidney stone, the kidney stone removal catheter comprising an irrigation lumen and a vacuum tube lumen, wherein the irrigation lumen communicates with a plurality of irrigation ports and the vacuum lumen is configured and sized for suction of a kidney stone or fragments of a kidney stone; and
   (b) a laser guide configured to be removably inserted into the vacuum lumen, wherein the laser guide comprises
   (i) a tubular body having distal and proximal opposing open ends and a lumen extending between the opens ends, wherein the lumen is configured to receive a laser device for fragmenting a kidney stone, and
   (ii) wings extending from a distal end segment of the tubular body for guiding the distal end segment of the tubular body in the vacuum lumen and creating flow gaps between the tubular body and an inner sidewall of the vacuum lumen such that the flow gaps are sized to allow suction of the kidney stone or fragments of the stone created by the laser device.

2. The kidney stone removal system of claim 1, wherein the tubular body is configured to not extend out of a distal end of the vacuum lumen when the tubular body is inserted completely into the vacuum lumen and placed in an operational position.

3. The kidney stone removal system of claim 1, wherein the guide consists of two wings to allow for the flow gaps to be of an adequate size for removal of the kidney stone or fragments of the stone created by the laser device.

4. The kidney stone removal system of claim 1, wherein the guide consists of three or four wings and wherein a circumferential distance is the same between each pair of neighboring wings.

5. The kidney stone removal system of claim 1, wherein the guide consists of three or four wings and wherein a circumferential distance between a first pair of the neighboring wings is different from a circumferential distance between a second pair of neighboring wings.

6. The kidney stone removal system of claim 5, wherein the first pair and second pair of neighboring wings share a common wing.

7. The kidney stone removal system of claim 1, wherein at least two of the gaps have different sizes.

8. The kidney stone removal system of claim 1, wherein each wing has a variable thickness that increases from a proximal end of the wing to a distal end of the wing along a longitudinal axis.

9. The kidney stone removal system of claim 1, wherein each wing has a longitudinal axis that is at an angle relative to a longitudinal axis of the tubular body.

10. The kidney stone removal system of claim 1, additionally comprising an actuator for moving the tubular body within the vacuum lumen.

11. The kidney stone removal system of claim 10, wherein the actuator comprises:
    (a) a biasing element; and
    (b) a shaft coupled to the tubular body, such that actuation of the biasing element causes the shaft to move the tubular body in a back-and-forth direction within the vacuum lumen.

12. The kidney stone removal system of claim 11, wherein the shaft is configured to be removably coupled to a proximal end of the tubular body.

13. The kidney stone removal system of claim 11, wherein the shaft is permanently attached to a proximal end of the tubular body.

14. The kidney stone removal system of claim 11, wherein the biasing element comprises a band coupled to a distal section of the shaft, and wherein the actuator additionally comprises a cylindrical housing coupled to the band and configured to receive the shaft, such that an inward compression and release of the band causes a part of the shaft to telescopically move into and out from the cylindrical housing.

15. The kidney stone removal system of claim 10, wherein the actuator comprises a first lever coupled to a second lever via a fulcrum bar.

16. The kidney stone removal system of claim 1, wherein the guide comprises two wings.

17. A kidney stone removal system, comprising:
    (a) a vacuum lumen; and
    (b) a laser guide configured to be removably inserted into the vacuum lumen, wherein the laser guide comprises
    (i) a tubular body having a lumen configured to receive a laser device, and
    (ii) wings extending from a distal end segment of the tubular body for guiding the distal end segment of the tubular body in the vacuum lumen and creating flow gaps between the tubular body and an inner side wall of the vacuum lumen,
wherein each wing comprises a middle segment having a rectangular shape which transitions into tapered end segments that slope downward into the tubular body.

18. A kidney stone removal system, comprising:
    (a) a vacuum lumen; and
    (b) a laser guide configured to be removably inserted into the vacuum lumen, wherein the laser guide comprises
    (i) a tubular body having a lumen configured to receive a laser device,
    (ii) wings extending from a distal end segment of the tubular body for guiding the distal end segment of the tubular body in the vacuum lumen and creating flow gaps between the tubular body and an inner side wall of the vacuum lumen, and
    (c) an actuator for moving the tubular body within the vacuum lumen wherein the actuator comprises a channel for receiving the laser device, the channel having a distal end configured to be in communication with the lumen of the tubular body and a proximal end configured to be in communication with a port of a handle device used for the operation of the kidney stone removal system.

19. A kidney stone removal system, comprising:
    (a) a kidney stone removal ureteroscope having a vacuum lumen for removal of kidney stone
    and irrigation channels for application of irrigation fluid; and
    (b) a laser guide configured to be removably inserted into the vacuum lumen, wherein the laser guide comprises
    (i) a tubular body having a lumen configured to receive a laser fiber, and
    (ii) two wings extending from a distal end segment of the tubular body for guiding the distal end segment of the tubular body in the vacuum lumen and creating flow gaps between the tubular body and an inner sidewall the vacuum lumen; and (c) a vision feature incorporated into a distal end of the ureteroscope.

20. The kidney stone removal system of claim 19, further comprising an actuator for moving the tubular body back and forth within the vacuum lumen.

21. The kidney stone removal system of claim 19, further comprising a self-resetting actuator for moving the tubular body back and forth within the vacuum lumen, the actuator comprising a first lever couple to a second lever by a fulcrum bar, wherein
  (i) the application of pressure to the first and second levers at a first position other than where the fulcrum bar is located causes the laser guide to move in a first direction from a position and removal of the pressure causes the laser guide to return to the position; and
  (ii) application of pressure to the first and second levers at a second position, different than the first position and other than where the fulcrum bar is located, causes the laser guide to move in a second, opposing direction, from the position and removal of the pressure causes the laser guide to return to the position.

22. The kidney stone removal system of claim 21, wherein the actuator additionally comprises
  a shaft coupled to the first lever and having a first end segment partially extending out of an opening of the first lever;
  a cylindrical housing coupled to the second lever for receiving a second, opposing end segment of the shaft, such that the shaft is configured to move telescopically, back-and-forth, within the cylindrical housing when pressure is applied to and release from the levers for actuation of the tubular body.

23. The kidney stone removal system of claim 22, wherein the first end segment of the shaft includes a head that is permanently affixed to a proximal end of the tubular body.

24. The kidney stone removal system of claim 22, wherein the first end segment of the shaft includes a head configured to be removably coupled to a proximal end of the tubular body.

25. The kidney stone removal system of claim 19, further comprises an actuator for moving the tubular body back-and-forth within the vacuum lumen, the actuator comprising
  an actuator distal end coupled to a proximal end of the tubular body;
  an actuator proximal end coupled to a handle used for the operation of the kidney stone removal ureteroscope; and
  a channel extending from the actuator proximal end to the actuator distal end for allowing the laser fiber to be inserted into the handle, through the channel, and into the tubular body.

26. The kidney stone removal system of claim 25, wherein the actuator is removably couple to the tubular body and/or the handle.

* * * * *

UNITED STATES PATENT AND TRADEMARK OFFICE
CERTIFICATE OF CORRECTION

Page 1 of 1

| | |
|---|---|
| PATENT NO. | : 12,256,989 B2 |
| APPLICATION NO. | : 18/827597 |
| DATED | : March 25, 2025 |
| INVENTOR(S) | : Matthew Yurek et al. |

It is certified that error appears in the above-identified patent and that said Letters Patent is hereby corrected as shown below:

In the Claims

In Column 17, at Line 10 (Claim 1), the word "tube" should be removed.

Signed and Sealed this
Ninth Day of December, 2025

John A. Squires
*Director of the United States Patent and Trademark Office*